US012240916B2

(12) United States Patent
Durocher et al.

(10) Patent No.: US 12,240,916 B2
(45) Date of Patent: Mar. 4, 2025

(54) INTRABODIES FOR REDUCING FUT8 ACTIVITY

(71) Applicant: National Research Council of Canada, Ottawa (CA)

(72) Inventors: Yves Durocher, Montreal (CA); Simon Joubert, Laval (CA)

(73) Assignee: National Research Council of Canada, Ottawa (CA)

(*) Notice: Subject to any disclaimer, the term of this patent is extended or adjusted under 35 U.S.C. 154(b) by 959 days.

(21) Appl. No.: 17/278,509

(22) PCT Filed: Sep. 20, 2019

(86) PCT No.: PCT/CA2019/051345
§ 371 (c)(1),
(2) Date: Mar. 22, 2021

(87) PCT Pub. No.: WO2020/056522
PCT Pub. Date: Mar. 26, 2020

(65) Prior Publication Data

US 2022/0033519 A1 Feb. 3, 2022

Related U.S. Application Data

(60) Provisional application No. 62/734,426, filed on Sep. 21, 2018.

(51) Int. Cl.
*C07K 16/40* (2006.01)
*C12N 15/62* (2006.01)

(52) U.S. Cl.
CPC .............. *C07K 16/40* (2013.01); *C12N 15/62* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 5,693,761 | A | 12/1997 | Queen et al. |
| 5,766,886 | A | 6/1998 | Studnicka et al. |
| 5,821,123 | A | 10/1998 | Studnicka |
| 5,859,205 | A | 1/1999 | Adair et al. |
| 5,869,619 | A | 2/1999 | Studnicka |
| 6,054,297 | A | 4/2000 | Carter et al. |
| 6,180,370 | B1 | 1/2001 | Queen et al. |
| 2007/0134759 | A1 | 6/2007 | Nishiya et al. |
| 2009/0208500 | A1 | 8/2009 | Joy et al. |

FOREIGN PATENT DOCUMENTS

| | | | |
|---|---|---|---|
| EP | 0626390 | B1 | 11/2001 |
| EP | 0519596 | B1 | 2/2005 |
| JP | 2001011097 | A * | 1/2001 |
| WO | WO94/02610 | A1 | 2/1994 |
| WO | WO1995/04069 | A1 | 2/1995 |
| WO | WO2003/046560 | A2 | 6/2003 |
| WO | WO2004/076670 | A1 | 9/2004 |
| WO | 2006133148 | | 12/2006 |
| WO | WO2008/070363 | A2 | 6/2008 |
| WO | 2009009086 | | 1/2009 |

OTHER PUBLICATIONS

Antibody Registry. AB_10886602 from Aviva Systems Biology Cat#ARP60784_P050, RRID:AB_10886602. (2014). Retrieved online on Jan. 18, 2024 from <URL:https://www.antibodyregistry.org/AB_10886602> (Year: 2014).*

Edwards et al. J. Mol. Biol. (2003) 334, 103â118 (Year: 2003).*

JP 2001011097 A English Translation retrieved from patents.google.com (Year: 2001).*

Lloyd et al. Protein Engineering, Design & Selection vol. 22 No. 3 pp. 159â168, 2009 (Year: 2009).*

Meyer et al. British Journal of Haematology, 2018, 180, 808â820 (Year: 2018).*

Vajdos et al. J Mol Biol. 2002. 320, 415-428 (Year: 2002).*

JP2001011097A—English Translation (Year: 2001).*

European Patent Office, Extended European Search Report, EP 19861827.4, Oct. 11, 2022.

Strebe N. et al., "Functional knockdown of VCAM-1 at the post-translational level with ER retained antibodies", Journal of Immunological Methods, Elsevier Science Publishers B.V., Amsterdam, NL, vol. 341, No. 1-2, Feb. 28, 2009, pp. 30-40.

Boldicke, Thomas et al., "Functional Inhibition of Transitory Proteins by Intrabody-Mediated Retention in the Endoplasmatic Reticulum", Methods, vol. 56, Jan. 1, 2012, pp. 338-350.

Boldicke, Thomas et al., "Novel highly efficient intrabody mediates complete inhibition of cell surface expression of the human vascular endothelial growth factor receptor-2 (VEGFR-2/KDR)", Journal of Immunological Methods, Elsevier Science Publishers B.V., Amsterdam, NL, vol. 300, No. 1-2, May 1, 2005, pp. 146-159.

Tragoolpua, Khajornsak et al., "Generation of functional scFv intrabody to abate the expression of CD147 surface molecule of 293A cells", BMC Biotechnology, Biomed Central Ltd., vol. 8, No. 1, Jan. 29, 2008, p. 5.

(Continued)

*Primary Examiner* — Zachary S Skelding
*Assistant Examiner* — Brianna K Swartwout
(74) *Attorney, Agent, or Firm* — Jessica Smith

(57) ABSTRACT

The present document describes an alpha-(1,6)-fucosyltransferase (FUT8) antibody, antigen binding domain thereof, or a fusion protein thereof, operable to inhibit FUT8 activity in a cell, and methods of producing recombinant proteins, in particular antibodies, having reduced fucosylation. The present document also describes methods of inhibiting expression and/or activity of a protein in a cell by expressing an antibody and/or a fusion protein operable to inhibit expression and/or activity of the protein. The antibody, antigen binding domain thereof, or fusion protein thereof may comprise a transmembrane domain of a protein resident in an endoplasmic reticulum (ER), a cis Golgi apparatus, a trans Golgi apparatus, or a combination thereof.

16 Claims, 11 Drawing Sheets

Specification includes a Sequence Listing.

(56) References Cited

OTHER PUBLICATIONS

Agrawal, P et al (Jun. 17, 2017) A Systems Biology Approach Identifies FUT8 as a Driver of Melanoma Metastasis. Cancer Cell 31: 804-819, ISSN: 1535-6108.
Noda, M et al (Jul. 5, 2018) Prognostic role of FUT8 expression in relation to p53 status in stage II and III colorectal cancer. PLOS ONE 13(17): e0200315, ISSN: 1932-6203.
Ito, Y. et al (2003) Expression of al,6-fucosyltransferase (FUT8) in papillary carcinoma of the thyroid: its linkage to biological aggressiveness and anaplastic transformation. Cancer Letters 200:167-172, ISSN: 1872-7980.
International Search Report, PCT/CA2019/051345, Nov. 25, 2019, Kerry Ferguson.
Supplemental Partial European Search Report of Corresponding European Application No. 19861827.4; Munich; Tina Saame; Jun. 6, 2022.
Lo et al. "Intracellular Antibodies (Intrabodies) and Their Therapeutic Potential", Handbook of Experimental Pharmacology, vol. 181, Jan. 1, 2008, pp. 343-373.
Kaiser et al. "Recent progress in generating intracellular functional antibody fragments to target and trace cellular components in living cells", Biochimica et Biophysica Acta (BBA)—Proteins and Proteomics, vol. 1844, No. 11, Nov. 2014, pp. 1933-1942.
Marschall et al. "Specific in vivo knockdown of protein function by intrabodies", MABS, vol. 7, No. 6, Nov./Dec. 2015, pp. 1010-1035.
Joubert et al. "Production of afucosylated antibodies in CHO cells by coexpression of an anti-FUT8 intrabody", Biotechnol Bioeng., vol. 119, No. 8, Aug. 2022, pp. 2206-2220.
Kabat et al. "Identical V Region Amino Acid Sequences and Segments of Sequences in Antibodies of Different Specifities", The Journal of Immunology, Sep. 1, 1991, vol. 147, No. 5, pp. 1709-1719.
Chothia et al. "Canonical Structures for the Hypervariable Regions of Immunoglobulins", J. Mol. Biol., 1987, pp. 901-917.
Hamers-Casterman et al. "Naturally occurring antibodies devoid of light chains", Nature, Jun. 3, 1993, vol. 363, pp. 446-448.
Nuttall et al. "Isolation and characterization of an IgNAR variable domain specific for the human mitochondrial translocase receptor Tom70", Eur. J. Biochem., Feb. 2003, vol. 270, pp. 3543-3554.
Jespers et al. "Aggregation-resistant domain antibodies selected on phage by heat denaturation", Nature Biotechnology, Sep. 2004, vol. 22, No. 9, pp. 1161-1165.
To et al. "Isolation of Monomeric Human VHS by a Phage Selection*", The Journal of Biological Chemistry, Dec. 16, 2005, vol. 280, No. 50, pp. 41395-41403.
Dumoulin et al. "Single-domain antibody fragments with high conformational stability", Protein Science, 2002, vol. 11, pp. 500-515.
Ghahroudi et al. "Selection and identification of Single domain antibody fragments from camel heavy-chain antibodies", FEBS Letters, 1997, vol. 414, pp. 521-526.
Li et al. "Pentabody-mediated antigen delivery induces antigen-specific mucosal immune response", Molecular Immunology, 2009, vol. 46, pp. 1718-1726.
Davis et al. "Affinity improvement of single antibody VH domains: residues in all three hypervariable regions affect antigen binding", Immunotechnology, 1996, vol. 2, pp. 169-179.
Hussack et al. "Engineered Single-Domain Antibodies with High Protease Resistance and Thermal Stability", PLoS ONE, Nov. 2011, vol. 6, No. 11, e28218.
Hussack et al. "Characterization of Single-Domain Antibodies with an Engineered Disulfide Bond*", Methods in Molecular Biology, vol. 911, pp. 417-429.
Nicaise et al. "Affinity transfer by CDR grafting on a nonimmunoglobulin scaffold", Protein Science, 2004, vol. 13, pp. 1882-1891.
Cronan "The *E. coli* bio Operon: Transcriptional Repression by an Essential Protein Modification Enzyme", Cell, Aug. 11, 1989, vol. 58, pp. 427-429.
Zhang et al. "Pentamerization of single-domain antibodies from phage libraries: a novel strategy for the rapid generation of high-avidity antibody reagents", J. Mol. Biol., 2004, vol. 335, pp. 49-56.
Zhang et al. "A Pentavalent Single-domain Antibody Approach to Tumor Antigen Discovery and the Development of Novel Proteomics Reagents", J. Mol. Biol., 2004, vol. 341, pp. 161-169.
Merritt et al. "AB5 toxins", Current Opinion in Structural Biology, 1995, vol. 5, pp. 165-171.
Zhu et al. "COMBODY: one-domain antibody multimer with improved avidity", Immunology and Cell Biology, 2010, vol. 88, pp. 667-675.
Nielsen et al. "Targeting of Bivalent Anti-ErbB2 Diabody Antibody Fragments to Tumor Cells Is Independent of the Intrinsic Antibody Affinity", Cancer Research, Nov. 15, 2000, vol. 60, pp. 6434-6440.
De Kruif et al. "Leucine Zipper Dimerized Bivalent and Bispecific scFv Antibodies from a Semi-synthetic Antibody Phage Display Library*", The Journal of Biological Chemistry, 1996, vol. 271, No. 13, pp. 7630-7634.
Ridgway et al. "'Knobs-into-holes' engineering of antibody CH3 domains for heavy chain heterodimerization", Protein Engineering, 1996, vol. 9, No. 7, pp. 617-621.
Bell et al. "Differential tumor-targeting abilities of three single-domain antibody formats", Cancer Letters, 2010, vol. 289, pp. 81-90.
Iqbal et al. "Kinetic analysis of novel mono- and multivalent VHH-fragments and their application for molecular imaging of brain tumours", British Journal of Pharmacology, 2010, vol. 160, pp. 1016-1028.
Shi et al. "Purification and Characterization of a Recombinant G-Protein-Coupled Receptor, *Saccharomyces cerevisiae* Ste2p, Transiently Expressed in HEK293 EBNA1 Cells", Biochemistry, 2005, vol. 44, No. 44, pp. 15705-15714.
Raymond et al. "A simplified polyethylenimine-mediated transfection process for large-scale and high-throughput applications", Methods, 2011, vol. 55, pp. 44-51.
Dorion-Thibaudeau et al. "Towards the development of a surface plasmon resonance assay to evaluate the glycosylation pattern of monoclonal antibodies using the extracellular domains of CD16a and CD64", Journal of Immunological Methods, 2014, vol. 408, pp. 24-34.
Delafosse et al. "Comparative study of polyethylenimines for transient gene expression in mammalian HEK293 and CHO cells", Journal of Biotechnology, 2016, vol. 227, pp. 103-111.
Von Kreudenstein et al. "Improving biophysical properties of a bispecific antibody scaffold to aid developability", mABs, 2013, vol. 5, No. 5, pp. 646-654.
Von Horsten et al. "Production of non-fucosylated antibodies by co-expression of heterologous GDP-6-deoxy-D-lyxo-4-hexulose reductase", Glycobiology, 2010, vol. 20, No. 12, pp. 1607-1618.
Kim et al. "Disulfide linkage engineering for improving biophysical properties of human VH domains", Protein Engineering, Design & Selection, 2012, vol. 25, No. 10, pp. 581-589.
Biocca et al. "Expression and targeting of intracellular antibodies in mammalian cells", The EMBO Journal, 1990, vol. 9, No. 1, pp. 101-108.
Boldicke et al. "Functional inhibition of transitory proteins by intrabody-mediated retention in the endoplasmatic reticulum", Methods, 2012, vol. 56, pp. 338-350.
Ihara et al. "Crystal structure of mammalian a1,6-fucosyltransferase, FUT8", Glycobiology, 2007, vol. 17, No. 5, pp. 455-466.
Schouten et al. "The C-terminal KDEL sequence increases the expression level of a single-chain antibody designed to be targeted to both the cytosol and the secretory pathway in transgenic tobacco", Plant Molecular Biology, 1996, vol. 30, pp. 781-793.
RabMAb AntiFUT8 [EPR14149] antibody (ab191571) [online]. Abcam [retrieved on Sep. 24, 2015]. Retrieved from the Internet: <URL: http://www.abcam.com/fut8epr14149antibodyab191571.html>.
Guglielmi et al. "Intrabody Expression In Eukaryotic Cells", Methods in molecular biology, 2009, vol. 562, pp. 195-203.
Vanhove et al. "Intracellular Expression in Pig Cells of ANTI-α1,3Galactosyltransferase Single-Chain FV Antibodies Reduces

(56) References Cited

OTHER PUBLICATIONS

GALα1,3GAL Expression and Inhibits Cytotoxicity Mediated by Anti-Galxenoantibodies1", Dec. 15, 1998, Transplantation, vol. 66, No. 11, pp. 1477-1485.

* cited by examiner

```
1H9VH    EVQLQQSGPELVKPGASVKMSCKASGYIFTDYVMHWVKQSNGKSLEWIGY
1D2VH    Q...KE...G..A.SQ.LSIT.TV..FSL.G.GVN..R.PP..G...L.M
5C9VH    Q...KE...G..A.SQ.LSIT.TV..FSL.G.GVN..R.PP..G...L.T

1H9VH    INPYNDYS-NYNQKFKGKATLTVDKSSNTAYMQLNSLTSEDSAVYFCARS
1D2VH    .--WG.G.TD..SAL.SRLSISK.N.KSQVFLKM...QTD.T.S.Y...D
5C9VH    .--WG.G.TD..SAL.SRLSISK.N.KTQVFLKMH..QTD.T.I.Y...G

1H9VH    ---G--DVW---LAYWGQGTLVTISA
1D2VH    FYD.--YLYA--MD......S..V.S
5C9VH    ---.YD.YFGYAMD......S..V.S


1H9VL    EFATMETDTLLLWVLLLWVPGSTGDIVLTQSPASLAISLGQRATISCRAS
1D2VL    ......SQ.QVFVYM...LS.VD....M...QKFMST...D.VSVT.K..
5C9VL    ......SQ.QVFVYM...LS.VD....M...QKFMSTVV.D.VSVT.K..

1H9VL    KSVSTSGYSYMHWYQQKPGQPPRLLIYLASNLESGVPARFSGSGSGTDFT
1D2VL    QN.G----..VA........S.KA...S..YRY....D..A.........
5C9VL    QN.G.N----VA........S.KA...S..YRY....D.LT.........

1H9VL    LNIHPVEEEDGATYYCQHSRELPWTFGGGT
1D2VL    .T.SN.QS..L.E.F..QYYTY.Y......
5C9VL    .TFSY.QS..L.E.F..QYYTY.Y......
```

FIG. 2

1H9scFv1:

1H9scFv3: TM B4GT1 | (GS)x | 1H9-VH | (GS)x | 1H9-VL | KDEL

1H9scFv4: SP | 1H9-VH | (GS)x | 1H9-VL | Myc-His

1H9scFv5: SP | 1H9-VH | (GS)x | 1H9-VL | (GS)x | TM+cyt CNX

| Construct | Fold reduction in fucosylation vs control |
|---|---|
| scFv1 | 6 |
| scFv3 | 6 |
| scFv4 | 3 |
| scFv5 | 8 |

SEQUENCE LISTING

<160> NUMBER OF SEQ ID NOS: 30

<210> SEQ ID NO 1
<211> LENGTH: 122
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 1

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Ser Tyr Tyr Cys Ala
                85                  90                  95

Arg Asp Phe Tyr Asp Gly Tyr Leu Tyr Ala Met Asp Tyr Trp Gly Gln
            100                 105                 110

Gly Thr Ser Val Thr Val Ser Ser Ala Ser
        115                 120
```

<210> SEQ ID NO 2
<211> LENGTH: 115
<212> TYPE: PRT
<213> ORGANISM: Artificial Sequence
<220> FEATURE:

<223> OTHER INFORMATION: Amino Acid
<220> FEATURE:
<223> OTHER INFORMATION: Mus Musculus

<400> SEQUENCE: 2

```
Asp Ile Val Met Thr Gln Ser Gln Lys Phe Met Ser Thr Ser Leu Gly
1               5                   10                  15

Asp Arg Val Ser Val Thr Cys Lys Ala Ser Gln Asn Val Gly Ser Tyr
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Ala Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Tyr Thr Tyr Pro Tyr
                85                  90                  95

Thr Phe Gly Gly Gly Thr Trp Ser Thr Arg Leu Ala Ser Trp Ala Phe
            100                 105                 110

Arg Ser Leu
        115
```

<210> SEQ ID NO 3
<211> LENGTH: 12
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 3

```
Gly Pro Gly Leu Val Ala Pro Ser Gln Ser Leu Ser
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: Amino Acid

<400> SEQUENCE: 4

```
Val Arg Gln Pro Pro Gly Lys Gly Leu Glu
1               5                   10
```

<210> SEQ ID NO 5
<211> LENGTH: 13
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 5

```
Gln Thr Asp Asp Thr Ala Ser Tyr Tyr Cys Ala Arg Asp
1               5                   10
```

<210> SEQ ID NO 6
<211> LENGTH: 12
<212> TYPE: PRT
<213> ORGANISM: Artificial Sequence
<220> FEATURE:

```
<223> OTHER INFORMATION: Amino Acid
<220> FEATURE:
<223> OTHER INFORMATION: Mus Musculus

<400> SEQUENCE: 6

Ser Gln Lys Phe Met Ser Thr Ser Leu Gly Asp Arg
1               5                   10


<210> SEQ ID NO 7
<211> LENGTH: 10
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 7

Tyr Gln Gln Lys Pro Gly Gln Ser Pro Lys
1               5                   10


<210> SEQ ID NO 8
<211> LENGTH: 13
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 8

Glu Tyr Phe Cys Gln Gln Tyr Tyr Thr Tyr Pro Tyr Thr
1               5                   10


<210> SEQ ID NO 9
<211> LENGTH: 121
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 9

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Thr Ile Trp Gly Asp Gly Ser Thr Asp Tyr Asn Ser Ala Leu Lys
    50                  55                  60

Ser Arg Leu Ser Ile Ser Lys Asp Asn Ser Lys Thr Gln Val Phe Leu
65                  70                  75                  80

Lys Met His Ser Leu Gln Thr Asp Asp Thr Ala Ile Tyr Tyr Cys Ala
                85                  90                  95

Arg Gly Gly Tyr Asp Asp Tyr Phe Gly Tyr Ala Met Asp Tyr Trp Gly
            100                 105                 110

Gln Gly Thr Ser Val Thr Val Ser Ser
        115                 120


<210> SEQ ID NO 10
<211> LENGTH: 107
<212> TYPE: PRT
```

<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 10

```
Asp Ile Val Met Thr Gln Ser Gln Lys Phe Met Ser Thr Val Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Leu Thr Gly
    50                  55                  60

Ser Gly Ser Gly Thr Asp Phe Thr Leu Thr Phe Ser Tyr Val Gln Ser
65                  70                  75                  80

Glu Asp Leu Ala Glu Tyr Phe Cys Gln Gln Tyr Tyr Thr Tyr Pro Tyr
                85                  90                  95

Thr Phe Gly Gly Gly Thr Lys Leu Glu Ile Lys
            100                 105
```

<210> SEQ ID NO 11
<211> LENGTH: 12
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 11

```
Gly Pro Gly Leu Val Ala Pro Ser Gln Ser Leu Ser
1               5                   10
```

<210> SEQ ID NO 12
<211> LENGTH: 10
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 12

```
Val Arg Gln Pro Pro Gly Lys Gly Leu Glu
1               5                   10
```

<210> SEQ ID NO 13
<211> LENGTH: 13
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 13

```
Gln Thr Asp Asp Thr Ala Ile Tyr Tyr Cys Ala Arg Gly
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 14

```
Ser Gln Lys Phe Met Ser Thr Val Val Gly Asp Arg
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 15

```
Tyr Gln Gln Lys Pro Gly Gln Ser Pro Lys
1               5                   10
```

<210> SEQ ID NO 16
<211> LENGTH: 13
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 16

```
Glu Tyr Phe Cys Gln Gln Tyr Tyr Thr Tyr Pro Tyr Thr
1               5                   10
```

<210> SEQ ID NO 17
<211> LENGTH: 119
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 17

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Thr Asp Tyr
            20                  25                  30

Val Met His Trp Val Lys Gln Ser Asn Gly Lys Ser Leu Glu Trp Ile
        35                  40                  45

Gly Tyr Ile Asn Pro Tyr Asn Asp Tyr Ser Asn Tyr Asn Gln Lys Phe
    50                  55                  60

Lys Gly Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Phe Cys
                85                  90                  95

Ala Arg Ser Gly Asp Val Trp Leu Ala Tyr Trp Gly Gln Gly Thr Leu
            100                 105                 110

Val Thr Ile Ser Ala Ala Ser
        115
```

<210> SEQ ID NO 18
<211> LENGTH: 106

<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 18

```
Asp Ile Val Leu Thr Gln Ser Pro Ala Ser Leu Ala Ile Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Gly Ala Thr Tyr Tyr Cys Gln His Ser Arg
                85                  90                  95

Glu Leu Pro Trp Thr Phe Gly Gly Gly Thr
            100                 105
```

<210> SEQ ID NO 19
<211> LENGTH: 12
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 19

```
Gly Pro Gly Leu Val Ala Pro Ser Gln Ser Leu Ser
1               5                   10
```

<210> SEQ ID NO 20
<211> LENGTH: 10
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 20

```
Val Arg Gln Pro Pro Gly Lys Gly Leu Glu
1               5                   10
```

<210> SEQ ID NO 21
<211> LENGTH: 13
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 21

```
Gln Thr Asp Asp Thr Ala Ile Tyr Tyr Cys Ala Arg Gly
1               5                   10
```

<210> SEQ ID NO 22
<211> LENGTH: 12
<212> TYPE: PRT

<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 22

Ser Gln Lys Phe Met Ser Thr Val Val Gly Asp Arg
1 5 10

<210> SEQ ID NO 23
<211> LENGTH: 10
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 23

Tyr Gln Gln Lys Pro Gly Gln Ser Pro Lys
1 5 10

<210> SEQ ID NO 24
<211> LENGTH: 13
<212> TYPE: PRT
<213> ORGANISM: Artificial Sequence
<220> FEATURE:
<223> OTHER INFORMATION: Amino Acid
<220> FEATURE:
<223> OTHER INFORMATION: Mus Musculus

<400> SEQUENCE: 24

Glu Tyr Phe Cys Gln Gln Tyr Tyr Thr Tyr Pro Tyr Thr
1 5 10

<210> SEQ ID NO 25
<211> LENGTH: 20
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 25

Trp Ile Met Leu Ile Leu Phe Ala Trp Gly Thr Leu Leu Phe Tyr Ile
1 5 10 15

Gly Gly His Leu
20

<210> SEQ ID NO 26
<211> LENGTH: 20
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 26

Leu Leu Val Ala Val Cys Ala Leu His Leu Gly Val Thr Leu Val Tyr
1 5 10 15

Tyr Leu Ala Gly
20

<210> SEQ ID NO 27

-continued

```
<211> LENGTH: 21
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 27

Trp Leu Trp Val Val Tyr Ile Leu Thr Val Ala Leu Pro Val Phe Leu
1               5                   10                  15

Val Ile Leu Phe Cys
            20


<210> SEQ ID NO 28
<211> LENGTH: 4
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 28

Lys Asp Glu Leu
1


<210> SEQ ID NO 29
<211> LENGTH: 22
<212> TYPE: PRT
<213> ORGANISM: Artificial Sequence
<220> FEATURE:
<223> OTHER INFORMATION: Amino Acid
<220> FEATURE:
<223> OTHER INFORMATION: Homo Sapiens

<400> SEQUENCE: 29

Met Arg Leu Pro Ala Gln Leu Leu Gly Leu Leu Met Leu Trp Val Ser
1               5                   10                  15

Gly Ser Ser Gly Asp Val
            20


<210> SEQ ID NO 30
<211> LENGTH: 14
<212> TYPE: PRT
<213> ORGANISM: Artificial Sequence
<220> FEATURE:
<223> OTHER INFORMATION: Amino Acid
<220> FEATURE:
<223> OTHER INFORMATION: Synthesized

<400> SEQUENCE: 30

Gly Gly Gly His His His His His His His His His His Gly
1               5                   10
```

INTRABODIES FOR REDUCING FUT8 ACTIVITY

CROSS-REFERENCE TO RELATED APPLICATIONS

This application is a U.S. National Phase application under 35 U.S.C. § 371 of PCT/CA2019/051345, filed Sep. 20, 2019, which claims priority from and the benefit of U.S. Provisional Patent Application No. 62/734,426 filed on Sep. 21, 2018, the specifications of which are hereby incorporated by reference in their entireties.

REFERENCE TO AN ELECTRONIC SEQUENCE LISTING

The contents of the electronic sequence listing (SEQ.txt; Size: 12,900 bytes and Date of Creation: Mar. 18, 2021) is herein incorporated by reference in its entirety.

BACKGROUND

(A) Field

The subject matter disclosed generally relates to antibodies, antigen binding fragment thereof, or fusion proteins operable to inhibit activity and/or expression of a protein in a cell. The subject matter disclosed more specifically relates to an alpha-(1,6)-fucosyltransferase (FUT8) antibody, an antigen binding fragment thereof, or a fusion protein thereof, operable to inhibit FUT8 activity in a cell, and methods of producing recombinant proteins, in particular antibodies, having reduced fucosylation. The subject matter disclosed also specifically relates to methods of inhibiting expression and/or activity of a protein in a cell by expressing an antibody and/or a fusion protein operable to inhibit expression and/or activity of the protein.

(b) Related Prior Art

Reducing fucosylation of recombinant proteins, especially therapeutic monoclonal antibodies (mAbs), is highly desirable for increasing effector functions [e.g. in antibody-dependent cell-mediated cytotoxicity (ADCC) and cell dependent cytotoxicity (CDC)] and to enhance their therapeutic efficacy.

FUT8 is the only fucosyltransferase that catalyzes the transfer of fucose from GDP-fucose to GlcNAc via α-1,6 linkage (medial Golgi). Therefore, the inhibition of FUT8 is a pertinent approach for reduction of fucosylation in vivo. Several approaches have been developed to reduce recombinant protein fucosylation, particularly of mAbs fucosylation. For example, FUT8 knockout (KO) CHO cells lines have been generated using zinc finger nucleases, meganucleases, siRNA, or the CRISPR/CAS9 system by companies such as Biowa, Genentech and Lonza. Also, the Co-expression of glycosylation enzyme beta1-4-N-acetylglucosaminyltransferase III (GnTIII) to generate altered glycoforms (Glycart), and the use of small FUT8 inhibitor molecules (Amgen), or of fucose diversion pathways [Probiogen: over-expression of the bacterial oxidoreductase GDP-6-deoxy-D-lyxo-4-hexulose reductase (RMD); Kyowa: GDP-d-mannose-4,6-dehydratase (GMD)] were used. However, the use of these systems is often expensive and represents a significant barrier to commercial and non-commercial production of recombinant proteins and mAbs.

Therefore, there is a need for alternative affordable technology for the production of CHO afucosylated proteins and/or antibodies.

SUMMARY

According to an embodiment, there is provided an alpha-(1,6)-fucosyltransferase (FUT8) antibody, an antigen binding fragment thereof, or a fusion protein thereof, comprising a variable region of a heavy ($V_H$) and a light ($V_L$) chain thereof, operable to inhibit FUT8 activity in a cell. The provided antibody or fusion protein thereof may comprise a heavy ($V_H$) and a light ($V_L$) chain or may be any antigen binding antibody or fragment capable of inhibiting FUT8 activity in a cell.

The fusion protein may comprise a transmembrane domain of a protein resident in an endoplasmic reticulum (ER), a cis Golgi apparatus, a trans Golgi apparatus, or a combination thereof.

According to another embodiment, there is provided a cell expressing the FUT8 antibody, antigen binding fragment thereof or fusion protein thereof, of the present invention.

According to another embodiment, there is provided a method for producing a recombinant antibody having reduced fucosylation comprising:

a) culturing a host cell expressing a FUT8 antibody, an antigen binding fragment thereof, or a fusion protein thereof, of the present invention, wherein the host cell expresses the recombinant antibody under conditions which permit the production of the recombinant antibody; and b) isolating the recombinant antibody.

According to another embodiment, there is provided a method for producing a recombinant protein having reduced fucosylation comprising:

a) culturing a host cell expressing a FUT8 antibody, an antigen binding fragment thereof, or a fusion protein thereof, of the present invention, wherein the host cell expresses the recombinant protein under conditions which permit the production of the recombinant protein; and b) isolating the recombinant protein.

According to another embodiment, there is provided a nucleic acid vector comprising a nucleotide sequence encoding an alpha-(1,6)-fucosyltransferase (FUT8) antibody, an antigen binding fragment thereof, or a fusion protein thereof according to the present invention.

According to another embodiment, there is provided a method for inhibiting expression and/or activity of a secreted protein in a cell comprising culturing a cell expressing an antibody, an antigen binding fragment thereof, or a fusion protein thereof comprising a variable region of a heavy ($V_H$) and a light ($V_L$) chain thereof, operable to inhibit expression and/or activity of the protein in the cell, the antibody, antigen binding fragment thereof, or the fusion protein thereof comprising a transmembrane domain of a protein resident in an endoplasmic reticulum (ER), a cis Golgi apparatus, a trans Golgi apparatus, or a combination thereof.

According to another embodiment, there is provided a FUT8 antibody, antigen binding fragment thereof, or a fusion protein thereof comprising a variable region of a heavy ($V_H$) and a light ($V_L$) chain thereof, wherein the variable region heavy ($V_H$) chain comprises an amino acid sequence comprising SEQ ID NO:1, and the variable region light ($V_L$) chain comprises an amino acid sequence comprising SEQ ID NO:2.

According to another embodiment, there is provided a FUT8 antibody, antigen binding fragment thereof, or a fusion protein thereof comprising a variable region of a heavy ($V_H$) and a light ($V_L$) chain thereof, wherein the variable region heavy ($V_H$) chain comprises CDR 1, CDR2 and CDR3 comprising an amino acid sequence comprising SEQ ID NO:3, SEQ ID NO:4, and SEQ ID NO:5, respectively;

and wherein the variable region light ($V_L$) chain comprises CDR 1, CDR2 and CDR3 comprising an amino acid sequence comprising SEQ ID NO:6, SEQ ID NO:7, and SEQ ID NO:8, respectively.

The FUT8 antibody, antigen binding fragment thereof, or fusion protein thereof may be antibody 1D2.

According to another embodiment, there is provided a FUT8 antibody, an antigen binding fragment thereof, or a fusion protein comprising a variable region of a heavy ($V_H$) and a light ($V_L$) chain thereof, wherein the variable region heavy ($V_H$) chain comprises an amino acid sequence comprising SEQ ID NO:9, and the variable region light ($V_L$) chain comprises an amino acid sequence comprising SEQ ID NO:10.

According to another embodiment, there is provided a FUT8 antibody, antigen binding fragment thereof, or a fusion protein thereof comprising a variable region of a heavy ($V_H$) and a light ($V_L$) chain thereof, wherein the variable region heavy ($V_H$) chain comprises CDR 1, CDR2 and CDR3 comprising an amino acid sequence comprising SEQ ID NO:11, SEQ ID NO:12, and SEQ ID NO:13, respectively;

and wherein the variable region light ($V_L$) chain comprises CDR 1, CDR2 and CDR3 comprising an amino acid sequence comprising SEQ ID NO:14, SEQ ID NO:15, and SEQ ID NO:16, respectively.

The FUT8 antibody, antigen binding fragment thereof, or fusion protein thereof may be antibody 5C9.

According to another embodiment, there is provided a FUT8 antibody, antigen binding fragment thereof, or a fusion protein thereof comprising a variable region of a heavy ($V_H$) and a light ($V_L$) chain thereof, wherein the variable region heavy ($V_H$) chain comprises an amino acid sequence comprising SEQ ID NO:17, and the variable region light ($V_L$) chain comprises an amino acid sequence comprising SEQ ID NO:18.

According to another embodiment, there is provided a FUT8 antibody, an antigen binding fragment thereof, or a fusion protein thereof comprising a variable region of a heavy ($V_H$) and a light ($V_L$) chain thereof, wherein the variable region heavy ($V_H$) chain comprises CDR 1, CDR2 and CDR3 comprising an amino acid sequence comprising SEQ ID NO:19, SEQ ID NO:20, and SEQ ID NO:21, respectively;

and wherein the variable region light ($V_L$) chain comprises CDR 1, CDR2 and CDR3 comprising an amino acid sequence comprising SEQ ID NO:22, SEQ ID NO:23, and SEQ ID NO:24, respectively.

The FUT8 antibody, antigen binding fragment thereof, or fusion protein thereof may be antibody 1H9.

The FUT8 antibody, antigen binding fragment thereof or fusion protein thereof may further comprise a transmembrane domain of a protein resident in an endoplasmic reticulum (ER), a cis Golgi apparatus, a trans Golgi apparatus, or a combination thereof.

The FUT8 antibody, antigen binding fragment thereof, or fusion protein thereof, of the present invention, or the cell of the present invention, or the method of the present invention, or the nucleic acid vector of the present invention, wherein the FUT8 antibody and/or the fusion protein further comprises an endoplasmic reticulum retention signal.

The FUT8 antibody, antigen binding fragment thereof or fusion protein thereof, of the present invention, the cell of the present invention, the method of the present invention, or the nucleic acid vector the present invention, wherein the FUT8 antibody may be an IgA, an IgD, an IgE, and IgG, an IgM, n Fab or combinations thereof.

The FUT8 antibody, antigen binding fragment thereof, or fusion protein thereof of the present invention, the cell of the present invention, the method of the present invention, or the nucleic acid vector of the present invention, wherein the antibody, antigen binding fragment or fusion protein may comprise a scFab, a scFv, a sdAb, or combinations thereof.

In the method of the present invention, the fusion protein may be a scFv.

The cell of the present invention, the method of the present invention, or the nucleic acid vector of the present invention, wherein the FUT8 antibody, antigen binding fragment thereof, or the fusion protein thereof may be the FUT8 antibody, antigen binding fragment thereof, or fusion protein thereof according to the present invention.

The FUT8 antibody, antigen binding fragment thereof, or fusion protein thereof of the present invention, the cell of the present invention, the method of the present invention, or the nucleic acid vector of the present invention, wherein the transmembrane domain may be chosen from a transmembrane domain of FUT8, a transmembrane domain of beta-1,4-galactosyltransferase 1 (B4GT1), and a transmembrane domain of human calnexin (hCNX).

The FUT8 antibody, antigen binding fragment thereof, or fusion protein thereof, cell or method according to the present invention, wherein the transmembrane domain of FUT8 may comprise an amino acid sequence comprising SEQ ID NO:25, the transmembrane domain of B4GT1 may comprise an amino acid sequence comprising SEQ ID NO:26, and the transmembrane domain of hCNX may comprise an amino acid sequence comprising SEQ ID NO:27.

The FUT8 antibody, antigen binding fragment thereof, or fusion protein thereof, cell or method according to the present invention, wherein the endoplasmic reticulum retention signal may comprise an amino acid sequence comprising SEQ ID NO:28.

The following terms are defined below.

The terms "intrabody" or "intrabodies" (from intracellular and antibody) refers to an antibody that works within the cell to bind to an intracellular protein. Introducing an antibody within the cell typically requires the expression of the antibody within the target cell. As a result, intrabodies are defined as antibodies that have been modified for intracellular localization. The terms are also used even when antibodies are produced in prokaryotes or other non-target cells.

The term "antibody", which is also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$)

results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk [Kabat et al, 1991, J Immunol (1991) 147(5):1709-1719; Chothia and Lesk 1987, J Mol Biol (1987) 196(4):901-917], define the "complementarity-determining regions" (CDR) based on sequence variability at the antigen-binding regions of the $V_H$ and $V_L$ domains. Chothia and Lesk 1987, J Mol Biol (1987) 196(4):901-917 define the "hypervariable loops" (H or L) based on the location of the structural loop regions in the $V_H$ and $V_L$ domains. These individual schemes define CDR and hypervariable loop regions that are adjacent or overlapping, those of skill in the antibody art often utilize the terms "CDR" and "hypervariable loop" interchangeably, and they may be so used herein. The CDR/loops are identified herein according to the Kabat scheme (i.e. CDR1, 2 and 3, for each variable region).

An "antibody fragment" or an "antigen binding domain", or an "antigen binding fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab')2, single-domain antibody (sdAb; a fragment composed of a single $V_L$ or $V_H$), and multivalent presentations of any of these. Antibody fragments such as those just described may require linker sequences, disulfide bonds, or other type of covalent bond to link different portions of the fragments; those of skill in the art will be familiar with the requirements of the different types of fragments and various approaches and various approaches for their construction.

In a non-limiting example, the antibody fragment may be an sdAb derived from naturally-occurring sources. Heavy chain antibodies of camelid origin (Hamers-Casterman et al, 1993, Nature 363: 446-448) lack light chains and thus their antigen binding sites consist of one domain, termed $V_H$H. sdAb have also been observed in shark and are termed $V_{NAR}$ (Nuttall et al, 2003, Eur. J. Biochem. 270: 3543-3554). Other sdAb may be engineered based on human Ig heavy and light chain sequences (Jespers et al, 2004, Nat. Biotechnol. 22: 1161-1165; To et al, 2005, J. Biol. Chem. 280: 41395-41403). As used herein, the term "sdAb" includes those sdAb directly isolated from $V_H$, $V_H$H, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb.

SdAb possess desirable properties for antibody molecules, such as high thermostability, high detergent resistance, relatively high resistance to proteases (Dumoulin et al, 2002, Protein Sci. 11: 500-15) and high production yield (Arbabi-Ghahroudi et al, 1997); they can also be engineered to have very high affinity by isolation from an immune library (Li et al, 2009, Mol. Immunol. 46: 1718-1726) or by in vitro affinity maturation (Davies & Riechmann, 1996, Immunotechnology 2: 169-79). Further modifications to increase stability, such as the introduction of non-canonical disulfide bonds (Hussack et al, 2011a,b; Kim et al, 2012, J. Biol. Chem. 286: 8961-8976), may also be brought to the sdAb.

A person of skill in the art would be well-acquainted with the structure of a single-domain antibody (see, for example, 3DWT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3.

The term "scFv" is intended to refer to single-chain variable fragment, although an scFv is not actually a fragment of an antibody, but instead is a fusion protein of the variable regions of the heavy ($V_H$) and light chains ($V_L$) of immunoglobulins, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This scFv protein retains the specificity of the original immunoglobulin, despite removal of the constant Fc regions and the introduction of the linker. ScFv molecules were created to facilitate phage display, where it is highly convenient to express the antigen-binding domain as a single peptide. As an alternative, scFv can be created directly from subcloned heavy and light chains derived from a hybridoma.

Divalent (or bivalent) scFvs (di-scFvs, bi-scFvs) can be engineered by linking two scFvs. This can be done by producing a single peptide chain with two $V_H$ and two $V_L$ regions, yielding tandem scFvs. Another possibility is the creation of scFvs with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. For example, a diabody drugs could be dosed much lower than other therapeutic antibodies and are capable of highly specific targeting of tumors in vivo. Still shorter linkers (one or two amino acids) lead to the formation of trimers, so-called triabodies or tribodies. Tetrabodies have also been produced. They exhibit an even higher affinity to their targets than diabodies.

All of these formats can be composed from variable fragments with specificity for two different antigens, in which case they are types of bispecific antibodies. The furthest developed of these are bispecific tandem di-scFvs, known as bi-specific T-cell engagers (BiTE antibody constructs).

The present invention further encompasses an antibody or fragment that is "humanized" using any suitable method known in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the CDR defined herein may be fused or grafted to a human variable region ($V_H$, or $V_L$), to other human antibody (IgA, IgD, IgE, IgG, and IgM), to other human antibody fragment framework regions (Fv, scFv, Fab) or to other proteins of similar size and nature onto which CDR can be grafted (Nicaise et al, 2004). In such a case, the conformation of said one or more than one hypervariable loop is likely preserved, and the affinity and specificity of the sdAb for its target (i.e., IGF1R) is likely minimally affected. CDR grafting is known in the art and is described in at least the following: U.S. Pat. Nos. 6,180,370, 5,693,761, 6,054,297, 5,859,205, and European Patent No. 626390. Veneering, also referred to in the art as "variable region resurfacing", involves humanizing solvent-exposed positions of the antibody or fragment; thus, buried nonhumanized residues, which may be important for CDR conformation, are preserved while the potential for immunological reaction against solvent-exposed regions is minimized. Veneering is known in the art and is described in at least the following: U.S. Pat. Nos. 5,869,619, 5,766,886, 5,821,123, and European Patent No. 519596. Persons of skill in the art would also be amply familiar with methods of preparing such humanized antibody fragments and humanizing amino acid positions.

The antibody, antigen binding fragment thereof, or fusion protein thereof, of the present invention may also comprise additional sequences to aid in expression, detection, localization or purification. Any such sequences or tags known to those of skill in the art may be used. For example, and without wishing to be limiting, the antibody or fragment thereof may comprise a targeting or signal sequence {for example, but not limited to ompA, a transmembrane domain of a protein resident in an endoplasmic reticulum (ER), a cis Golgi apparatus, a trans Golgi apparatus, or a combination thereof [e.g. a transmembrane domain of FUT8, a transmembrane domain of beta-1,4-galactosyltransferase 1 (B4GT1), and a transmembrane domain of human calnexin (hCNX)], an endoplasmic reticulum retention signal (KDEL)}, a detection/purification tag (for example, but not limited to c-Myc, His5, or His6), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody, antigen binding fragment thereof, or fusion protein thereof of the present invention may also be in a multivalent display format, also referred to herein as multivalent presentation. Multimerization may be achieved by any suitable method of known in the art. For example, and without wishing to be limiting in any manner, multimerization may be achieved using self-assembly molecules such as those described in Zhang et al (2004a, Mol. Biol. 341: 161-169; and 2004b, J. Mol. Biol. 335: 49-56) and WO2003/046560, where pentabodies are produced by expressing a fusion protein comprising the antibody or fragment thereof of the present invention and the pentamerization domain of the B-subunit of an AB5 toxin family (Merritt & Hol, 1995, Curr. Opin. Struct. Biol. 5: 165-171). A multimer may also be formed using the multimerization domains described by Zhu et al. (2010, Immunol. Cell Biol. 88: 667-675); this form, referred to herein as a "combody" form, is a fusion of the antibody or fragment of the present invention with a coiled-coil peptide resulting in a multimeric molecule (Zhu et al., 2010, Immunol. Cell Biol. 88: 667-675). Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielson et al, 2000, Cancer Res. 60: 6434-6440), c-jun/Fos interaction (de Kruif & Logtenberg, 1996, J. Biol. Chem. 271: 7630-7634), "Knob into holes" interaction (Ridgway et al, 1996, Protein Eng. 9: 617-621).

Another method known in the art for multimerization is to dimerize the antibody or fragment thereof using an Fc domain, for example, but not limited to human Fc domains. The Fc domains may be selected from various classes including, but not limited to, IgG, IgM, or various subclasses including, but not limited to IgG1, IgG2, etc. In this approach, the Fc gene in inserted into a vector along with the sdAb gene to generate a sdAb-Fc fusion protein (Bell et al, 2010, Cancer Lett. 289: 81-90; Iqbal et al, 2010, Br. J. Pharmacol. 160: 1016-28); the fusion protein is recombinantly expressed then purified. For example, and without wishing to be limiting in any manner, multivalent display formats may encompass chimeric or humanized formats of antibodies $V_H$H linked to an Fc domain, or bi or tri-specific antibody fusions with two or three antibodies $V_H$H recognizing unique epitopes. Such antibodies are easy to engineer and to produce, can greatly extend the serum half-life of sdAb, and may be excellent tumor imaging reagents (Bell et al., 2010, Cancer Lett. 289: 81-90).

The Fc domain in the multimeric complex as just described may be any suitable Fc fragment known in the art. The Fc fragment may be from any suitable source; for example, the Fc may be of mouse or human origin. In a specific, non-limiting example, the Fc may be the mouse Fc2b fragment or human Fc1 fragment (Bell et al, 2010, Cancer Lett. 289: 81-90; Iqbal et al, 2010, Br. J. Pharmacol. 160: 1016-28). The Fc fragment may be fused to the N-terminal or C-terminal end of the $V_H$H or humanized versions of the present invention.

Each subunit of the multimers described above may comprise the same or different antibodies or fragments thereof of the present invention, which may have the same or different specificity. Additionally, the multimerization domains may be linked to the antibody or antibody fragment using a linker, as required; such a linker should be of sufficient length and appropriate composition to provide flexible attachment of the two molecules, but should not hamper the antigen-binding properties of the antibody.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 2 illustrates the sequence of the mAb sequence of the selected hybridomas.

It will be noted that throughout the appended drawings, like features are identified by like reference numerals.

DETAILED DESCRIPTION

Figure 1:
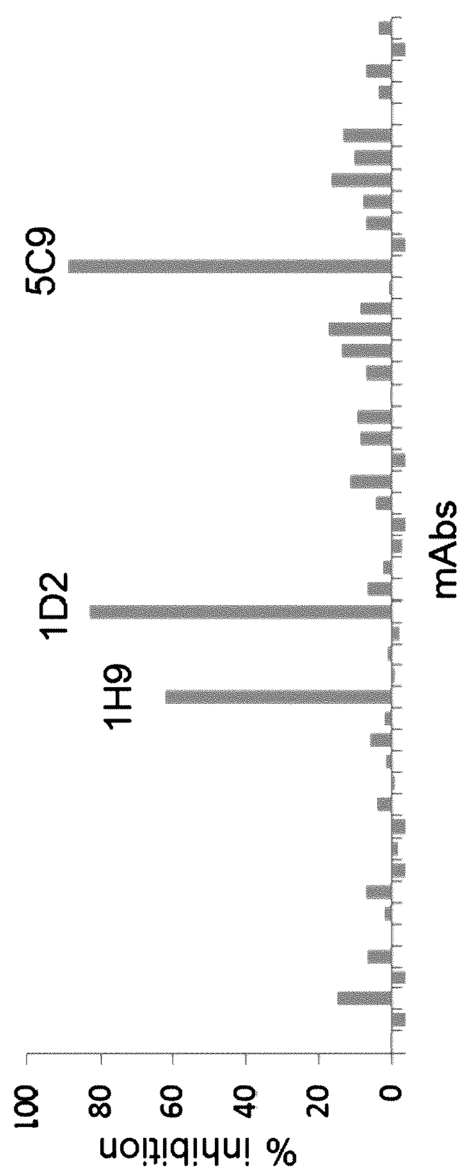
FIG. 1 illustrates the inhibition of FUT8 activity by 50 mAbs produced from tested hybridomas. The 1H9, 1D2 and 5C9 were selected as potent inhibitors.

The present invention is directed to a technology for inhibiting the activity and/or expression of a protein in vivo. In embodiments, the technology uses intrabodies directed to the protein of interest to inhibit the activity and/or expression thereof. More specifically, in embodiments, the intrabodies are directed to FUT8, to inhibit the fucosyltransferase activity of this enzyme, and therefore reduce overall fucosylation of the proteins produced therein.

In a first embodiment there is disclosed an alpha-(1,6)-fucosyltransferase (FUT8) antibody, antigen binding fragment thereof, or a fusion protein thereof, comprising a variable region of a heavy ($V_H$) and a light ($V_L$) chain thereof, operable to inhibit FUT8 activity in a cell. The provided antibody or fusion protein thereof may comprise a heavy ($V_H$) and a light ($V_L$) chain or may be any antigen binding antibody or fragment capable of inhibiting FUT8 activity in a cell.

The FUT8 antibody, antigen binding fragment thereof, or the fusion protein thereof may comprise a transmembrane domain of a protein resident in an endoplasmic reticulum (ER), a cis Golgi apparatus, a trans Golgi apparatus, or a combination thereof.

According to other embodiments of the FUT8 antibody, antigen binding fragment thereof, or fusion protein thereof of the present invention, the transmembrane domain is chosen from a transmembrane domain of FUT8, a transmembrane domain of beta-1,4-galactosyltransferase 1 (B4GT1), and a transmembrane domain of human calnexin (hCNX). For example, the transmembrane domain of FUT8 may comprise an amino acid sequence comprising SEQ ID NO:25, the transmembrane domain of B4GT1 may comprise an amino acid sequence comprising SEQ ID NO:26, and the transmembrane domain of hCNX may comprise an amino acid sequence comprising SEQ ID NO:27.

According to an embodiment of the FUT8 antibody, antigen binding fragment thereof, or fusion protein thereof, comprising a variable region of a heavy ($V_H$) and a light ($V_L$) chain thereof, the variable region heavy ($V_H$) chain may comprise an amino acid sequence comprising SEQ ID NO:1, and the variable region light ($V_L$) chain may comprise an amino acid sequence comprising SEQ ID NO:2.

According to another embodiment of the FUT8 antibody, antigen binding fragment thereof, or fusion protein thereof, comprising a variable region of a heavy ($V_H$) and a light ($V_L$) chain thereof, the variable region heavy ($V_H$) chain may comprise CDR 1, CDR2 and CDR3 comprising an amino acid sequence comprising SEQ ID NO:3, SEQ ID NO:4, and SEQ ID NO:5, respectively; and the variable region light ($V_L$) chain comprises CDR 1, CDR2 and CDR3 comprising an amino acid sequence comprising SEQ ID NO:6, SEQ ID NO:7, and SEQ ID NO:8, respectively.

According to an embodiment, the FUT8 antibody, antigen binding fragment thereof, or fusion protein thereof may be antibody 1D2.

According to another embodiment of the FUT8 antibody, antigen binding fragment thereof, or a fusion protein thereof, comprising a variable region of a heavy ($V_H$) and a light ($V_L$) chain thereof, the variable region heavy ($V_H$) chain may comprise an amino acid sequence comprising SEQ ID NO:9, and the variable region light ($V_L$) chain may comprise an amino acid sequence comprising SEQ ID NO:10.

According to another embodiment of the FUT8 antibody, antigen binding fragment thereof, or a fusion protein thereof, comprising a variable region of a heavy ($V_H$) and a light ($V_L$) chain thereof, the variable region heavy ($V_H$) chain may comprise CDR 1, CDR2 and CDR3 comprising an amino acid sequence comprising SEQ ID NO:11, SEQ ID NO:12, and SEQ ID NO:13, respectively; and the variable region light ($V_L$) chain may comprise CDR 1, CDR2 and CDR3 comprising an amino acid sequence comprising SEQ ID NO:14, SEQ ID NO:15, and SEQ ID NO:16, respectively.

According to an embodiment, the FUT8 antibody, antigen binding fragment thereof, or fusion protein thereof may be antibody 5C9.

According to another embodiment of the FUT8 antibody, antigen binding fragment thereof, or fusion protein thereof, comprising a variable region of a heavy ($V_H$) and a light ($V_L$) chain thereof, the variable region heavy ($V_H$) chain may comprise an amino acid sequence comprising SEQ ID NO:17, and the variable region light ($V_L$) chain may comprise an amino acid sequence comprising SEQ ID NO:18.

According to another embodiment of the FUT8 antibody, antigen binding fragment thereof, or fusion protein thereof, comprising a variable region of a heavy ($V_H$) and a light ($V_L$) chain thereof, the variable region heavy ($V_H$) chain may comprise CDR 1, CDR2 and CDR3 comprising an amino acid sequence comprising SEQ ID NO:19, SEQ ID NO:20, and SEQ ID NO:21, respectively; and the variable region light ($V_L$) chain may comprise CDR 1, CDR2 and CDR3 comprising an amino acid sequence comprising SEQ ID NO:22, SEQ ID NO:23, and SEQ ID NO:24, respectively.

According to another embodiment, the FUT8 antibody, antigen binding fragment thereof, or fusion protein thereof may be antibody 1H9.

According to other embodiments of the FUT8 antibody, antigen binding fragment thereof, or fusion protein thereof, of the present invention, the FUT8 antibody and/or the fusion protein may further comprises an endoplasmic reticulum retention signal. For example, the endoplasmic reticulum retention signal is comprising an amino acid sequence comprising SEQ ID NO:28—KDEL.

According to other embodiments of the FUT8 antibody, antigen binding fragment thereof, or fusion protein thereof of the present invention, the FUT8 antibody may be an IgA, an IgD, an IgE, and IgG, an IgM, an Fab or combinations thereof.

According to other embodiments of the FUT8 antibody, antigen binding fragment thereof, or fusion protein thereof of the present invention, the fusion protein may be a scFab, a scFv, a sbAb, or combinations thereof.

According to another embodiment, there is disclosed a cell expressing the FUT8 antibody, antigen binding fragment thereof, or a fusion protein thereof of the present invention.

According to another embodiment, there is disclosed a method for producing a recombinant antibody having reduced fucosylation comprising:

a) culturing a host cell expressing the FUT8 antibody, antigen binding fragment thereof or fusion protein thereof, of the present invention, wherein the host cell expresses the recombinant antibody under conditions which permit the production of the recombinant antibody; and b) isolating the recombinant antibody.

According to another embodiment, there is disclosed a method for producing a recombinant protein having reduced fucosylation comprising:

a) culturing a host cell expressing a FUT8 antibody, antigen binding fragment thereof, or a fusion protein thereof, of the present invention, wherein the host cell expresses the recombinant protein under conditions which permit the production of the recombinant protein; and b) isolating the recombinant protein.

According to an embodiment, the fusion protein is a scFv.

According to an embodiment, the FUT8 antibody, antigen binding fragment thereof, or said fusion protein thereof, is the FUT8 antibody or fusion protein according to the present invention.

According to an embodiment, the said transmembrane domain is chosen from a transmembrane domain of FUT8, a transmembrane domain of beta-1,4-galactosyltransferase 1 (B4GT1), and a transmembrane domain of human calnexin (hCNX). The transmembrane domain of FUT8 may comprise an amino acid sequence comprising SEQ ID NO:25, the transmembrane domain of B4GT1 may comprise an amino acid sequence comprising SEQ ID NO:26, and the transmembrane domain of hCNX may comprise an amino acid sequence comprising SEQ ID NO:27.

According to other embodiments of the FUT8 antibody, antigen binding fragment thereof, or fusion protein thereof of the present invention, the FUT8 antibody and/or the fusion protein may further comprises an endoplasmic reticulum retention signal. For example, the endoplasmic reticulum retention signal is comprising an amino acid sequence comprising SEQ ID NO:28—KDEL.

According to another embodiment, there is disclosed a nucleic acid vector comprising a nucleotide sequence encoding an alpha-(1,6)-fucosyltransferase (FUT8) antibody, antigen binding fragment thereof, or a fusion protein thereof, comprising a variable region of a heavy ($V_H$) and a light ($V_L$) chain thereof, operable to inhibit FUT8 activity in a cell, the FUT8 antibody and/or the fusion protein comprising a transmembrane domain of a protein resident in an endoplasmic reticulum (ER), a cis Golgi apparatus, a trans Golgi apparatus, or a combination thereof.

According to an embodiment, the FUT8 antibody, antigen binding fragment thereof, and/or said fusion protein thereof is the FUT8 antibody or fusion protein according to the present invention.

According to an embodiment, the said transmembrane domain is chosen from a transmembrane domain of FUT8, a transmembrane domain of beta-1,4-galactosyltransferase 1 (B4GT1), and a transmembrane domain of human calnexin (hCNX). The transmembrane domain of FUT8 may comprise an amino acid sequence comprising SEQ ID NO:25, the transmembrane domain of B4GT1 may comprise an amino acid sequence comprising SEQ ID NO:26, and the transmembrane domain of hCNX may comprise an amino acid sequence comprising SEQ ID NO:27.

According to other embodiments of the FUT8 antibody, antigen binding fragment thereof, or fusion protein thereof of the present invention, the FUT8 antibody, antigen binding fragment thereof, or the fusion protein thereof may further comprises an endoplasmic reticulum retention signal. For example, the endoplasmic reticulum retention signal is comprising an amino acid sequence comprising SEQ ID NO:28—KDEL.

According to another embodiment, there is disclosed a cell expressing an antibody and/or a fusion protein comprising a variable region of a heavy ($V_H$) and a light ($V_L$) chain thereof, operable to inhibit expression and/or activity of a protein in the cell, the antibody and/or the fusion protein comprising a transmembrane domain of a protein resident in an endoplasmic reticulum (ER), a cis Golgi apparatus, a trans Golgi apparatus, or a combination thereof.

According to an embodiment, the FUT8 antibody, antigen binding fragment thereof, or said fusion protein thereof is the FUT8 antibody or fusion protein according to the present invention.

According to an embodiment, the said transmembrane domain is chosen from a transmembrane domain of FUT8, a transmembrane domain of beta-1,4-galactosyltransferase 1 (B4GT1), and a transmembrane domain of human calnexin (hCNX). The transmembrane domain of FUT8 may comprise an amino acid sequence comprising SEQ ID NO:25, the transmembrane domain of B4GT1 may comprise an amino acid sequence comprising SEQ ID NO:26, and the transmembrane domain of hCNX may comprise an amino acid sequence comprising SEQ ID NO:27.

According to other embodiments of the FUT8 antibody, antigen binding fragment thereof, or fusion protein thereof of the present invention, the FUT8 antibody, antigen binding fragment thereof, or the fusion protein thereof may further comprises an endoplasmic reticulum retention signal. For example, the endoplasmic reticulum retention signal is comprising an amino acid sequence comprising SEQ ID NO:28—KDEL.

According to another embodiment, there is disclosed a method for inhibiting expression and/or activity of a secreted protein in a cell comprising culturing a cell expressing an antibody and/or a fusion protein comprising a variable region of a heavy ($V_H$) and a light ($V_L$) chain thereof, operable to inhibit expression and/or activity of the protein in the cell, the antibody and/or the fusion protein comprising a transmembrane domain of a protein resident in an endoplasmic reticulum (ER), a cis Golgi apparatus, a trans Golgi apparatus, or a combination thereof.

According to an embodiment, the FUT8 antibody, antigen binding fragment thereof, or said fusion protein thereof is the FUT8 antibody, antigen binding fragment thereof, or fusion protein thereof according to the present invention.

According to an embodiment, the transmembrane domain is chosen from a transmembrane domain of FUT8, a transmembrane domain of beta-1,4-galactosyltransferase 1 (B4GT1), and a transmembrane domain of human calnexin (hCNX). The transmembrane domain of FUT8 may comprise an amino acid sequence comprising SEQ ID NO:25, the transmembrane domain of B4GT1 may comprise an amino acid sequence comprising SEQ ID NO:26, and the transmembrane domain of hCNX may comprise an amino acid sequence comprising SEQ ID NO:27.

According to other embodiments of the FUT8 antibody, antigen binding fragment thereof, or fusion protein thereof of the present invention, the FUT8 antibody, antigen binding fragment thereof, or the fusion protein thereof may further comprises an endoplasmic reticulum retention signal. For example, the endoplasmic reticulum retention signal may comprise an amino acid sequence comprising SEQ ID NO:28—KDEL.

The present invention will be more readily understood by referring to the following examples which are given to illustrate the invention rather than to limit its scope.

Example 1

Soluble FUT8 Expression and Purification

A pTT5 expression vector (Shi 2005, Biochemistry, 44(48), 15705-15714) encoding a codon-optimized soluble and secreted FUT8 (sFUT8) enzyme (aa 87-575; UniProtKB #Q9BYC5) with a N-terminal signal peptide (SEQ ID NO: 29—MRLPAQLLGLLMLWVSGSSGDV) and a C-terminal polyhistidine tag (SEQ ID NO: 30—GGGHHHHHHHHHHG) was transiently transfected in 293-6E cells as described previously (Raymond 2011, Methods (San Diego, Calif.), 55(1), 44-51). Culture medium was harvested 5 days post-transfection and purified by immobilized metal affinity chromatography as described in Dorion-Thibaudeau et al. 2014, J Immunol Methods, 408, 24-34.

Example 2

Anti-sFUT8 Monoclonal Antibody Generation

Animal immunization. Four six-week old female A/J mice (The Jackson Laboratory, Bar Harbor, ME) were bled (pre-immune serum) and injected intraperitoneally and subcutaneously with 100 μg of sFUT8 antigen emulsified in Titermax adjuvant (Cedarlane Labs, Burlington, ON) at day 0 and at day 21. Blood was collected in microvette CB 300Z (Sarstedt, Montreal, QC) at day 31 or 38, and serum was stored at −20° C. until further use.

ELISA (serum titer determination). Pre- and post-immune sera titers of animals were assessed by ELISA. Unless otherwise stated, all incubations were performed at room temperature. Briefly, half-area 96-well plates (Costar® #3690) were coated with 25 μl per well of immunogen at 20 μg/ml in PBS and incubated overnight at 4° C. Microplates were washed three times in PBS and blocked for 30 min with PBS containing 1% bovine serum albumin (BSA, Sigma® Cat #A7030). Blocking buffer was removed and 25 μl of serial dilutions of sera samples were added. After a 2-h incubation, microplates were washed 4 times with PBS-Tween 20 0.05% and 25 μl of a 1/5,000 dilution of alkaline phosphatase conjugated goat anti-mouse IgG (H+L) (#115-056-062, Jackson Immunoresearch®, Cedarlane, Burlington, ON) in blocking buffer was added. After a 1-h incubation, microplates were washed 4 times and 25 μl of p-nitrophenyl phosphate (pNPP) substrate (Sigma-Aldrich Canada Co.®, Oakville, ON) at 1 mg/ml in carbonate buffer at pH 9.6 was added and further incubated for 30 min. Absorbance was read at 405 nm using a SpectraMax® plate reader (Molecular Devices®, Sunnyvale, CA). All pre-immune bleeds were negative and all post-immune bleeds were very strong (above 1/12800) on recombinant protein. A final intraperitoneal booster injection using 100 μg of recombinant protein in PBS was done 3 days prior to fusion experiment.

Fusion of the harvested spleen cells. All manipulations were done under sterile conditions. Spleen cells were harvested in Iscove's Modified Dulbecco's medium (IMDM, Gibco® Cat. #31980-030) and fused to NSO myeloma cell line using polyethylene glycol. Spleen cells and myeloma cells were washed in IMDM, counted in RBC lysing buffer (Sigma, Cat #7757-100ML) and mixed together at a 5:1 ratio. Pelleted cells were fused together by adding 1 ml of a 50% solution of PEG 4000 (EMD-Millipore® Cat #9727-2) in PBS preheated at 37° C. drop-wise over one minute, and incubated at 37° C. for an additional 90 sec. The reaction was stopped by addition of 30 ml of IMDM at 22° C. over 2 min. After a 10 min incubation, freshly fused cells were spun at 233×g for 10 min. Cells were washed once in IMDM supplemented with 10% heat inactivated FBS (Sigma Cat #F1051) and suspended at a concentration of $2\times10^5$ input myeloma cells per ml in HAT selection medium (IMDM containing 20% heat inactivated FBS, penicillin-streptomycin (Sigma® Cat #P7539), 1 ng/ml mouse IL-6 (Biolegend Cat #575706), HAT media supplement (Sigma® Cat #H0262) and L-glutamine (Hy-Clone® Cat #SH30034.01) and incubated at 37° C., 5% $CO_2$. The next day, hybridoma cells were washed and suspended at a concentration of 2-3×$10^5$ input myeloma cells per ml in semi-solid medium D (StemCell Technologies® Cat. #03804) supplemented with 5% heat inactivated FBS, 1 ng/ml mouse IL-6 and 10 μg/ml FITC-F(ab')2 Goat anti-mouse IgG (Jackson® #115-056-062). The cell mixture was plated in Omnitray® dish (Nunc® cat #242811) and further incubated for 6-7 days at 37° C., 5% $CO_2$. Fluorescent secretor clones were then transferred using a mammalian cell clone picker (ClonepixFL®, Molecular Devices®) into sterile 96-w plates (Costar® #3595) containing 200 μl of IMDM supplemented with 20% heat inactivated FBS, penicillin-streptomycin, 1 ng/ml mouse IL-6, HT media supplement (Sigma® Cat #H0137) and L-glutamine and incubated for 2-3 days at 37° C., 5% $CO_2$.

Screening. Hybridoma supernatant were screened by ELISA to detect specific binders. To this end, 96-wells half-area plates (Costar® #3690) were coated with 25 μl of sFUT8 at 20 μg/ml or an irrelevant control protein at 5 μg/ml in PBS and incubated overnight at 4° C. Microplates were washed 3 times with PBS, blocked with PBS-BSA 1%, and 25 μl of hybridoma supernatant were added and incubated at 37° C., 5% $CO_2$ for 2 hours. Plates were washed 4 times with PBS-Tween 20 0.05% and incubated for one hour at 37° C., 5% $CO_2$ with 25 μl of secondary antibody alkaline phosphatase conjugated F(ab')2 goat anti-mouse IgG (Jackson Immunoresearch #115-056-062) diluted 1/5000 in blocking buffer. After 4 washes with PBS-Tween 20 0.05%, 25 μl of a 1 mg/ml pNPP substrate solution was added and further incubated for one hour at 37° C. OD405 nm measurements were done using a microplate reader (Spectramax® 340 PC, Molecular Devices®). Hits were confirmed using alkaline phosphatase conjugated F(ab')2 goat anti-mouse IgG Fc gamma specific (Jackson Immunoresearch® #115-056-071) and 50 mAbs were selected for further characterization.

Recloning of hybridomas. Selected hybridoma were recloned by limiting dilution to ensure their monoclonality.

FUT8 enzyme inhibition assay. The assay is shown below:

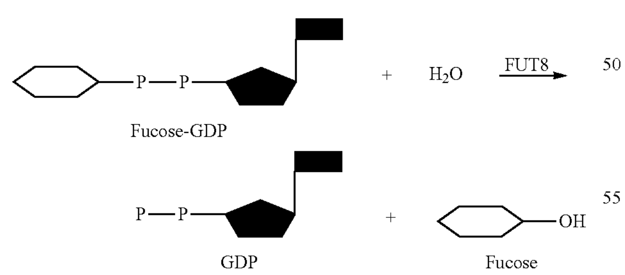

The assay reaction was done using 2 mM FUT8 enzyme, 60 mM Fucose-GDP, purified mAb (1-5 μM) in DPBS and 30 mM MES buffer pH7.0 for 2 hours at room temperature. The % inhibition was determined based on the changes in signals for the GDP-fucose and GDP measured by LC-MS relative to control experiments (i.e. substrate alone, and substrate+enzyme in absence of mAb). The results of this assay are shown in FIG. 1 and the mAbs 1H9, 1D2 and 5C9 were selected as potent FUT8 inhibitors. The sequence of these mAbs are shown in FIG. 2.

Example 3

Making of Recombinant Anti-FUT8

Figure 3:
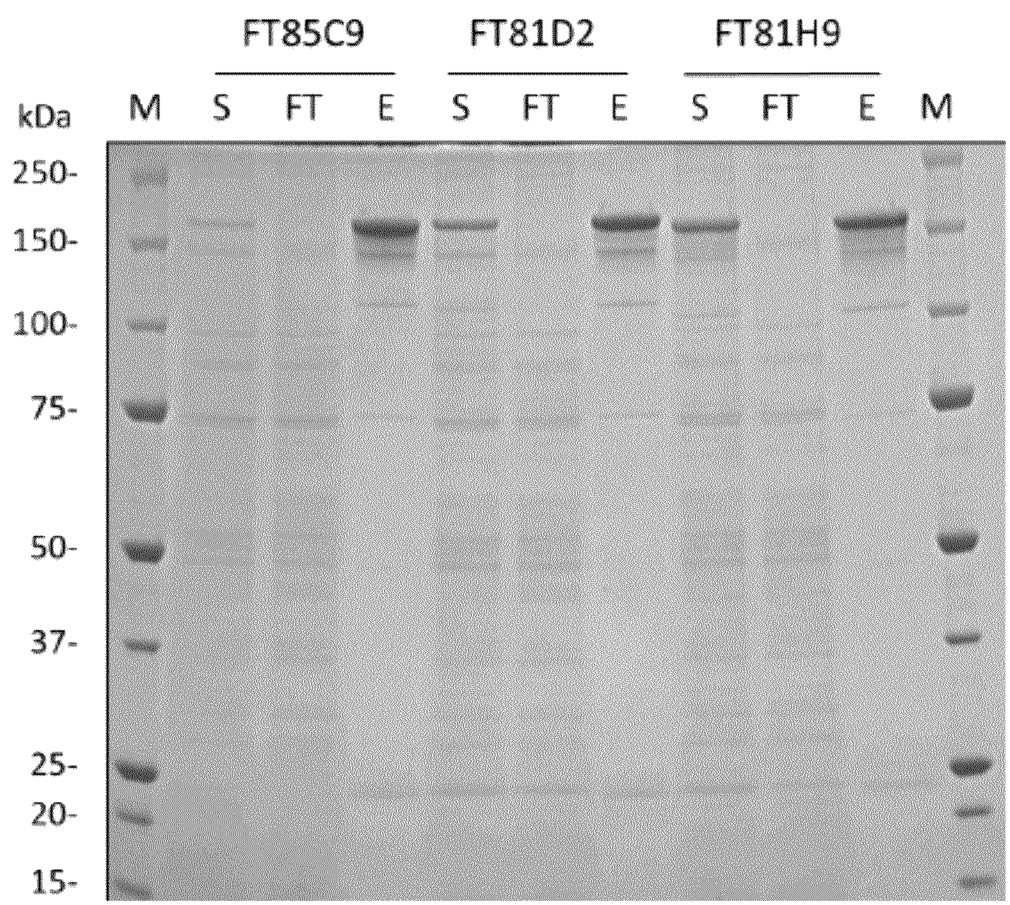
FIG. 3 illustrates the expression of recombinant mAbs produced in CHO-3E7 cells from the $V_H$ and $V_L$ of the 3 mAbs 1H9, 1D2 and 5C9 cloned into PTT5-CH123 (hIgG1) and PTT5-kappa vectors. (S: supernatant), (FT: flow-through) and (E: elution).

Now referring to FIG. 3, the $V_H$ and $V_L$ regions of the candidate mAbs 1H9, 1D2 and 5C9 were sequenced, synthesized and cloned into the pTT5 vector in-frame with a constant domain of a human IgG1 heavy chain (comprising CH1, CH2 and CH3 regions) or in-frame with a constant domain of a human kappa light chain, and recombinant mAbs were produced in CHO-3E7 cells by transient transfection according to Delafosse et al 2016, J Biotechnol, 227, 103-111.

Example 4

Cell Surface Fucosylation Measurement by Flow Cytometry

Figure 4:
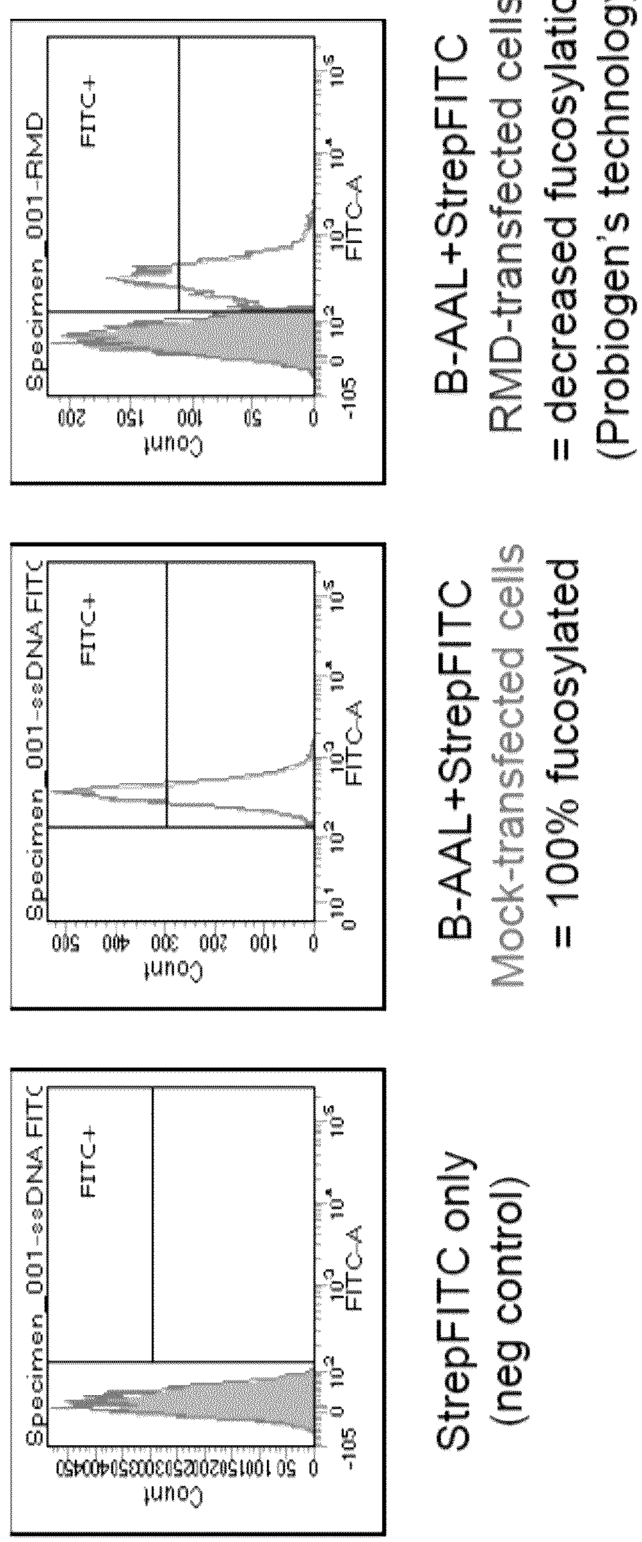
FIG. 4 illustrates that mock transfected cells are fully fucosylated, while cells transfected with RMD show decreased fucosylation.
Figure 5:
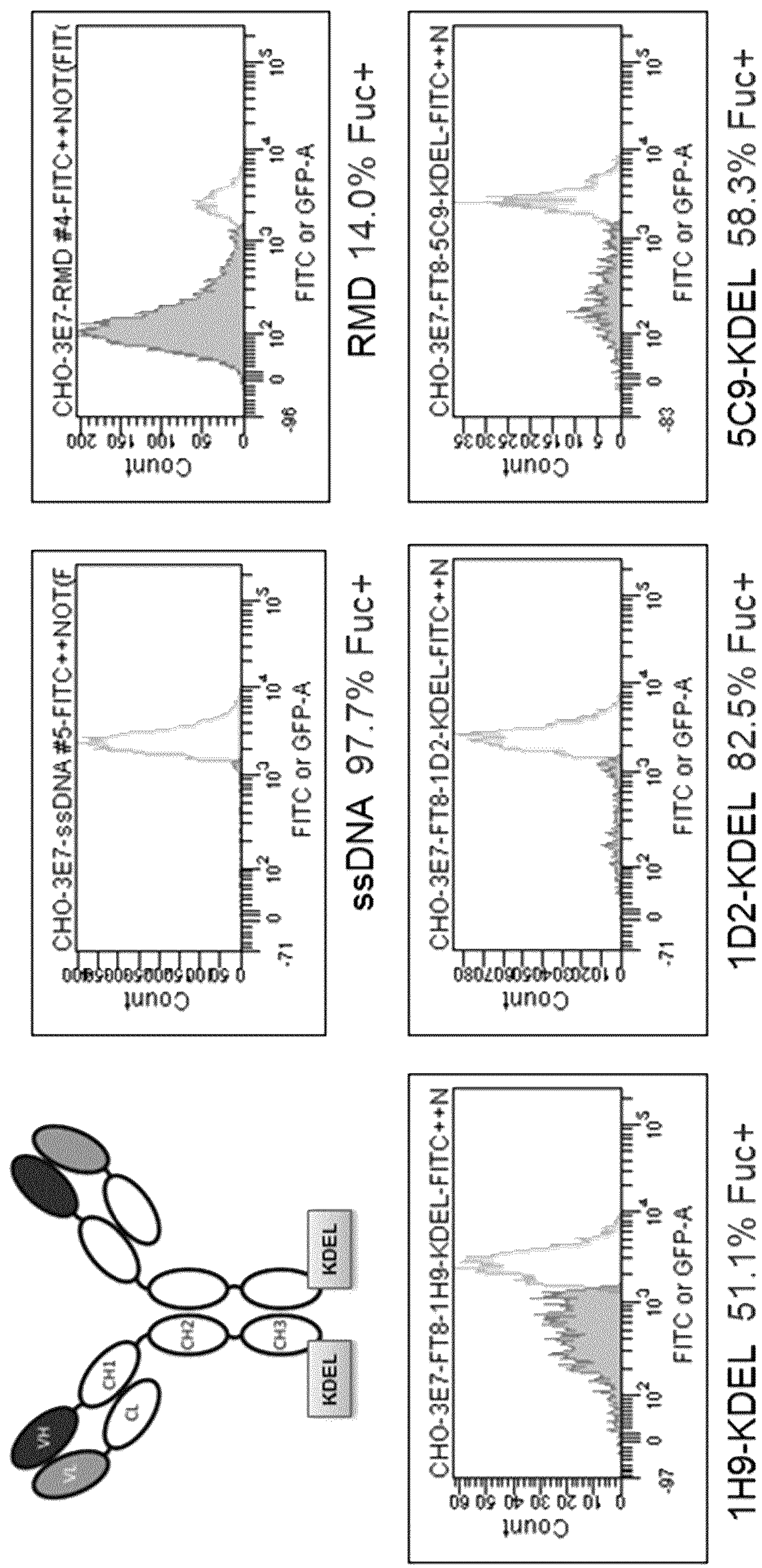
FIG. 5 illustrates that mAbs 1H9, 1D2 and 5C9 fused with a retention signal (KDEL) are able to inhibit fucosylation with various efficacies when transiently expressed in CHO cells.

Approximately 0.75×$10^6$ CHO cells were centrifuged (280 g for 3 min) and resuspended in 1 ml PBS containing 0.5% (w/v) BSA. Ten μl of biotinylated Aleuria Aurantia Lectin, (bAAL; Vector Laboratories® Inc. cat #B-1395) was added to the cell suspension followed by a 30 min incubation on ice. Cells were centrifuged and resuspended into 1 ml PBS containing 0.5% (w/v) BSA. To the cell suspension, 10 μl of Streptavidin-FITC was added followed by 30 min incubation on ice. Cells were washed once with 50 μl PBS/0.5% (w/v) BSA, resuspended in 500 μl of PBS/0.5% (w/v) BSA and filtered through a 30 μm mesh Nytex® filter prior to flow cytometry analysis. Now referring to FIG. 4, the results show that mock transfected cells are fully fucosylated, while cells transfected with RMD show decreased fucosylation. Now referring to FIG. 5, the results show that mAbs 1H9, 1D2 and 5C9 fused with a retention signal (KDEL) are able to inhibit fucosylation with various efficacies when transiently expressed in CHO cells.

Example 5

Western Blot Analysis Using Lectin

Following protein separation by SDS-PAGE and transfer to a nitrocellulose membrane, protein fucosylation was revealed by incubating the membrane in the presence of biotinylated LCA (10 μg/mL) or AAL (10 μg/mL) lectins diluted in blocking solution for 1 h at RT. Following extensive washing, the membranes were incubated with Streptavidin-HRP for 1 h at RT. Membranes were then revealed using Biorad®'s ECL detection kit (Clarity™ Western ECL Substrate).

Example 6

Inhibition of FUT8 Activity with Intrabodies

Figure 6:
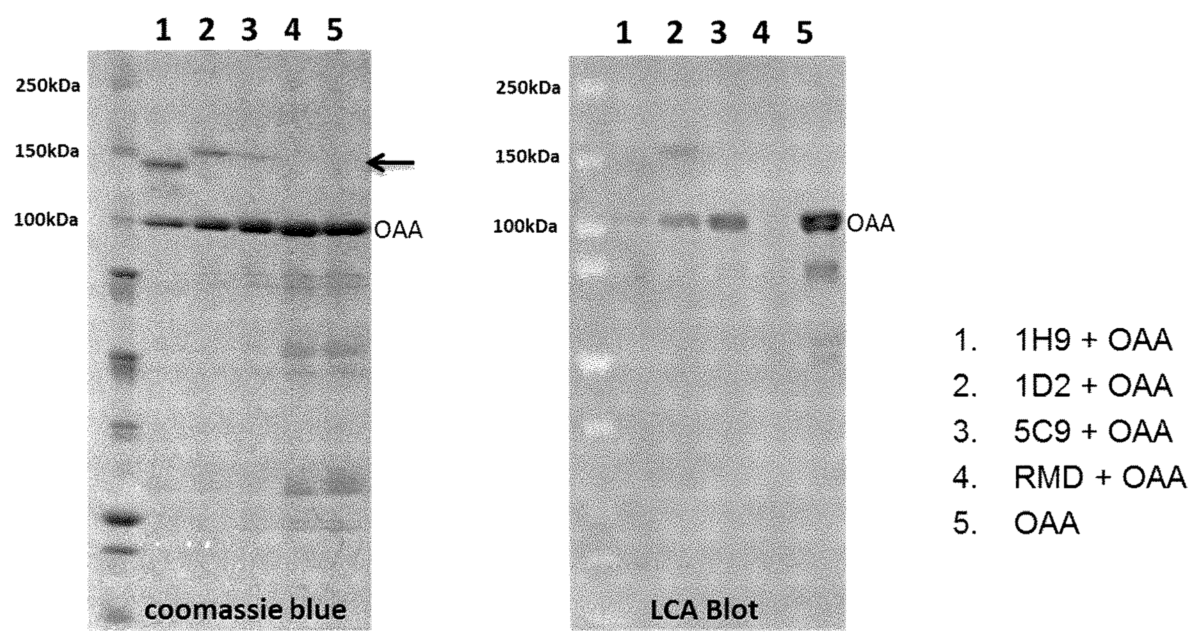
FIG. 6 illustrates recombinant FUT8 antibodies 1H9, 1D2 and 5C9 with a C-terminal KDEL sequence of the heavy chain coexpressed with a one-arm monoclonal antibody (OAA) in CHO cells. The results show that the C-terminal KDEL sequence is not sufficient to fully retain the anti-FUT8 mAbs within the cells as we can clearly detect them in the supernatants.

Now referring to FIG. 6, the recombinant FUT8 antibodies (1H9, 1D2 & 5C9) with a C-terminal KDEL sequence of the heavy chain were coexpressed with a one-arm monoclonal antibody (OAA) in CHO cells constructed using the Azymetric Het-Fc scaffold (Von Kreudenstein 2013, MAbs 5(5):646-654). The OAA was selected because of its smaller size (100 kDa) compared to the anti-FUT8 mabs (~150 kDa; arrow), allowing for their discrimination on the gel. As a positive control for reduced fucosylation, the OAA antibody was co-expressed with RMD encoding plasmid (Von Horsten 2010, Glycobiology 20(12):1607-1618). Five days later, supernatants were harvested and analyzed by SDS-PAGE and lectin-blot detection using biotinylated Lens Culinaris agglutinin (bLCA).

The Coomassie-blue stained SDS-PAGE shows that the OAA was present in the supernatant for all co-transfection experiment. However, the gel also indicate that the C-terminal KDEL sequence is not sufficient to fully retain the anti-FUT8 mabs within the cells as we can clearly detect them in the supernatants (as shown by the "intrabodies" arrow at ~150 kDa). The corresponding bLCA lectin-blot shows that fucosylation of the OAA is easily detected in the control lane (transfection of OAA only) while it is strongly reduced by RMD co-expression. For the anti-FUT8 intrabodies, reduction of fucosylation was most apparent when OAA was co-transfected with 1H9.

Example 7

Surface Plasmon Resonance (SPR)

Figure 7:
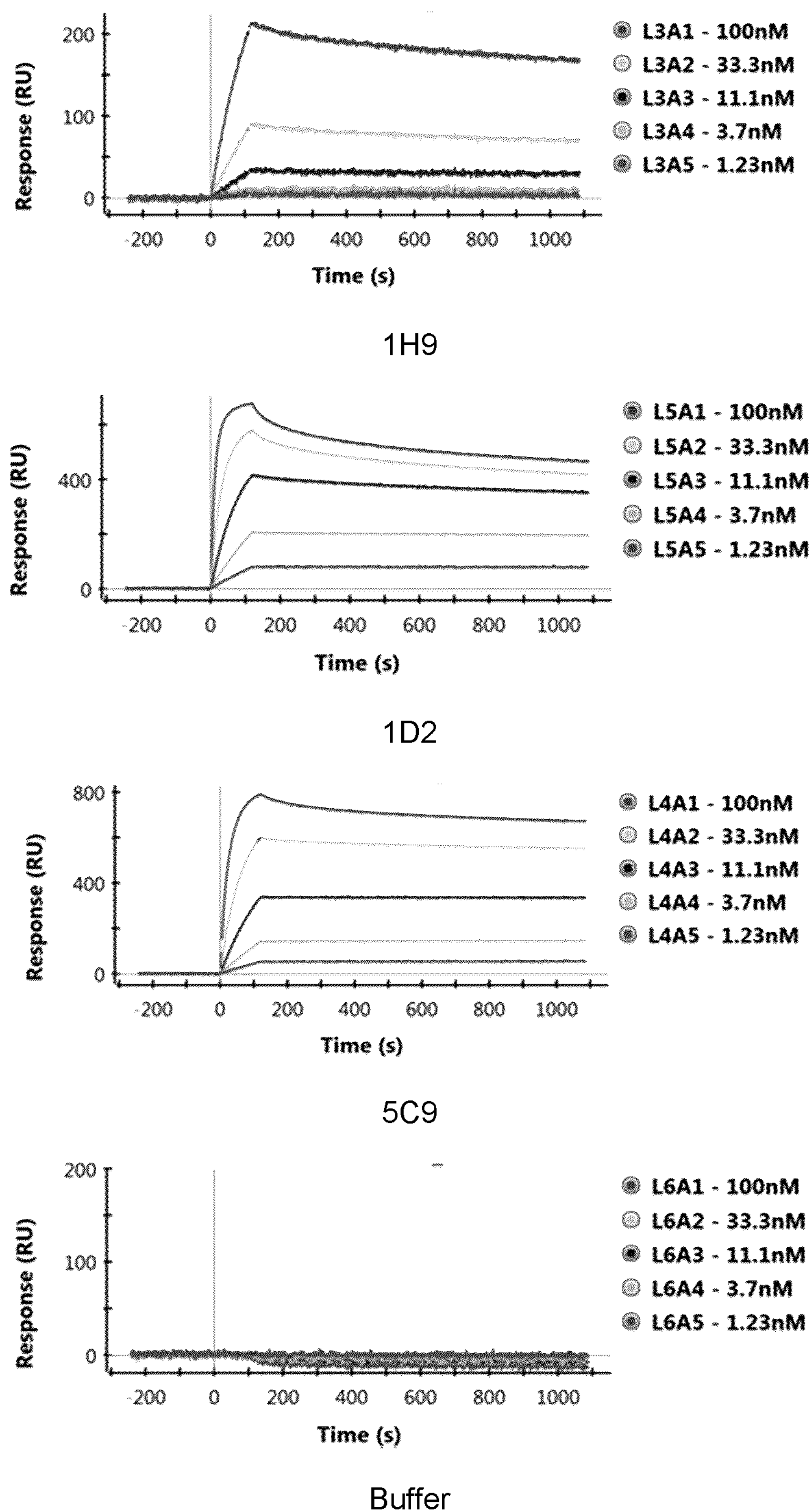
FIG. 7 illustrates the binding of FUT8 to indirectly capture anti-FUT8 antibody 1H9, 1D2 or 5C9 as determined by surface plasmon resonance using a BioRad® Proteon® (Mississauga, ON).

Now referring to FIG. 7, the binding of FUT8 to indirectly capture anti-FUT8 antibody was determined by surface plasmon resonance using a BioRad® Proteon® (Mississauga, ON). Each of the recombinant FUT8 antibodies 1H9, 1D2 & 5C9 was tested. PBS containing 0.05% Tween 20 (Teknova® Inc., Hollister, CA) and 3.4 mM EDTA was used as a running buffer at 25° C. An anti-human Fc capture surface was made with goat anti-human-Fc polyclonal antibody (Jackson ImmunoResearch®, West Grove, PA) immobilized to approximately 5000 RUs on a GLC sensorchip using standard amine coupling of a 25 μg/mL solution in 10 mM NaOAc pH 4.5. For the binding assay, approximately 1000 RUs of each anti-FUT8 antibody to be tested was captured onto the anti-human Fc surface by injecting 5 μg/mL anti-FUT8 solution for 240 seconds at flow rate 25 μL/min. This was followed by injection of a FUT8 dilution series (100/33.3/11.1/3.7/1.23 nM) and PBST running buffer for referencing. 120 second injections of each FUT8 concentration were used at a flow rate of 50 μL/min and with 900 second dissociation. Surfaces were regenerated with two 18 secs pulses of 0.85% phosphoric acid at a flow rate 100 μL/min. Sensorgrams were double referenced using mock-activated reference spots, and data were analyzed within BioRad Proteon evaluation software v3.1.

Example 8

Cell Surface Fucosylation Measurement by Flow Cytometry

Figure 8:
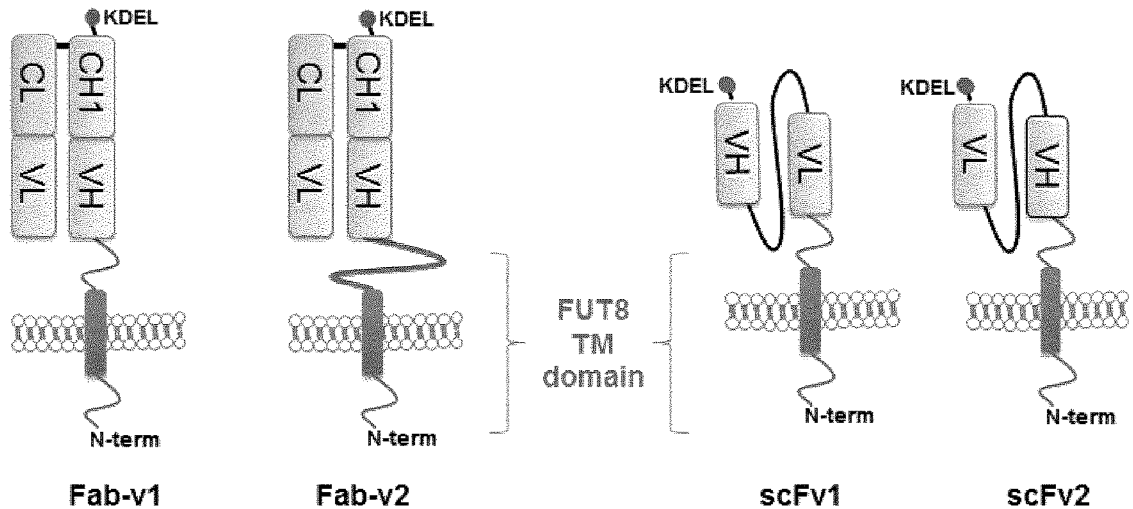
FIG. 8 illustrates a graphical representation of Fab and scFv versions of the mAbs of the present invention, which were prepared.
Figure 9:
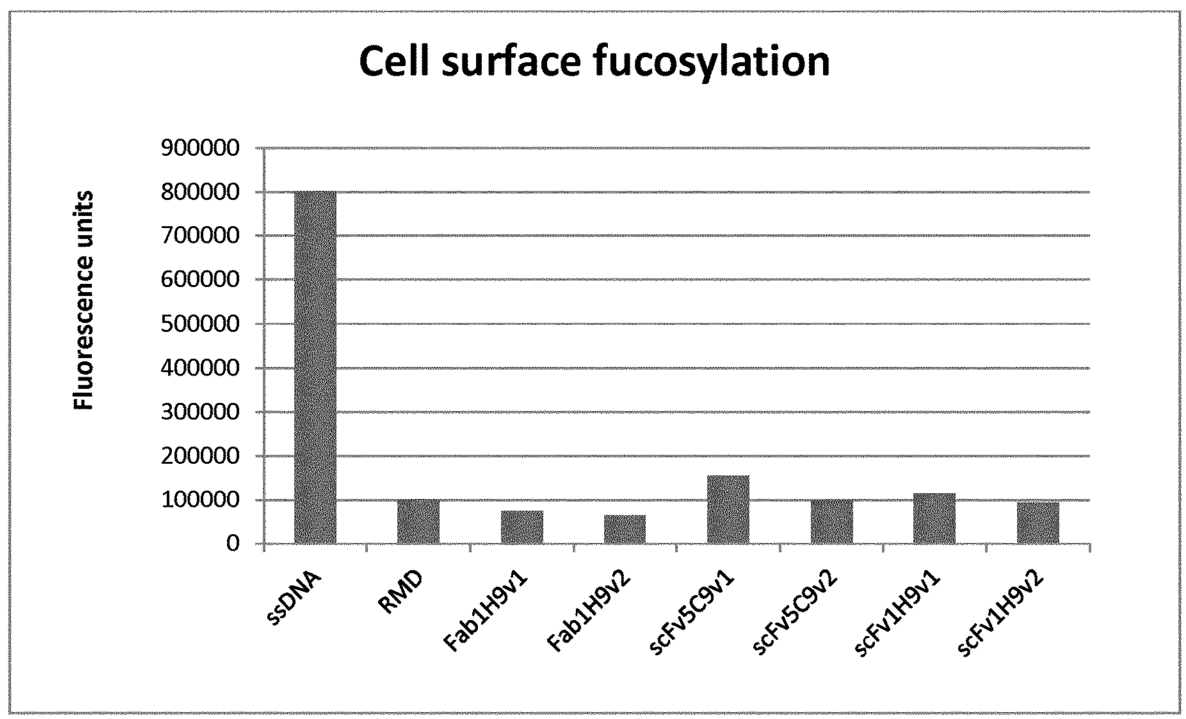
FIG. 9 illustrates the measured cell surface fucosylation levels as evidenced by labeling with biotinylated Aleuria Aurantia Lectin (AAL) and detection with fluorescein isothiocyanate (FITC)-streptavidin, of the of Fab and scFv versions of the mAbs illustrated in FIG. 8.

Now referring to FIGS. 8 and 9. FIG. 8 shows graphical representations of Fab and scFv versions of the mAbs of the present invention, which were prepared. FIG. 9 shows the measured cell surface fucosylation levels as evidenced by labeling with biotinylated AAL and detection with FITC-streptavidin. Total cell surface fluorescence level inhibited by membrane anchored scFv's and Fab variants of the mAbs 1H9 and 5C9, as was measured by flow cytometry. The %-positive cells is multiplied by the mean fluorescence intensity to get the total cell-surface fucosylation level as measured by lectin. The results show that the 1H9 is the most efficient to decrease fucosylation. However, Fab cannot be used to produce afucosylated mAb because of light chain scrambling.

Example 9

Test of Additional scFv Constructs

Figure 10:
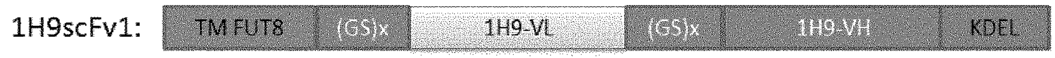
FIG. 10 illustrates schematic representations of additional constructs according to the present invention that were prepared.
Figure 11:
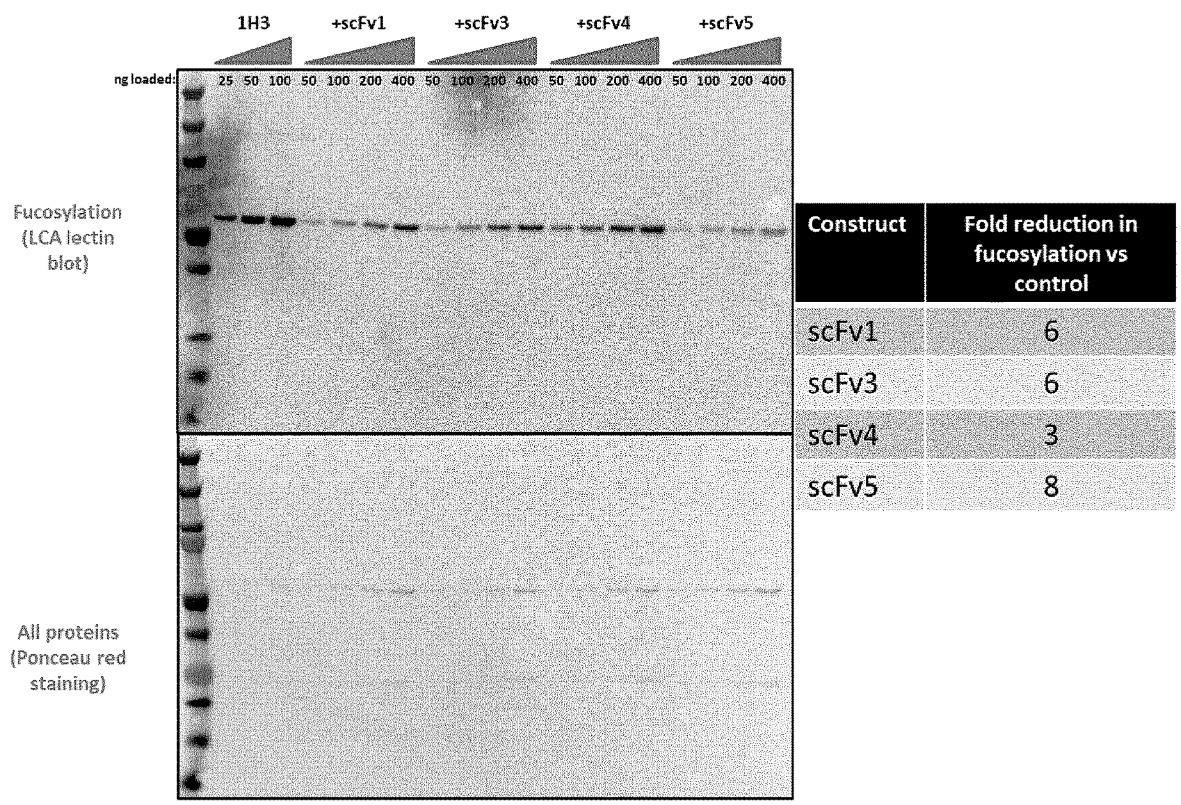
FIG. 11 illustrates that cells expressing the identified constructs of FIG. 10 were able to reduce fucosylation to various levels, especially the scFv5 construct bearing a signal peptide (SP), the calnexin transmembrane and cytoplasmic domains, which was able to reduce fucosylation by 8-fold.

FIG. 10 illustrates schematic representations of additional constructs according to the present invention that were prepared. FIG. 11 shows that cells expressing the identified constructs were able to reduce fucosylation to various levels, especially the scFv5 construct bearing a signal peptide (SP) and the calnexin transmembrane and cytoplasmic domain was able to reduce fucosylation by 8-fold.

While preferred embodiments have been described above and illustrated in the accompanying drawings, it will be evident to those skilled in the art that modifications may be made without departing from this disclosure. Such modifications are considered as possible variants comprised in the scope of the disclosure.

Example 10

Test of Additional scFv Sequences

Figure 12:
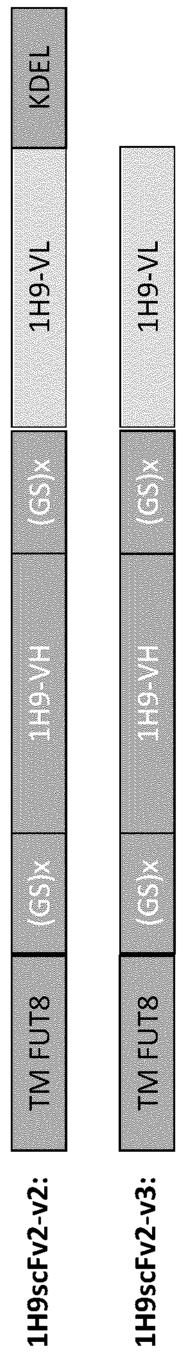
FIG. 12 illustrates schematic representations of constructs that were prepared with and without the KDEL sequence according to embodiments of the present invention.

FIG. 12 illustrates schematic representations of additional constructs that were prepared with and without the KDEL sequence according to embodiments of the present invention.

Table 1 shows the comparison between FUT8 reactivity measured by ELISA versus the inhibitory activity of FUT8 activity, for specific anti-FUT8 mAbs obtained from hybridoma sequences which were selected based on corresponding in vitro FUT8 activity inhibition percentage.

TABLE 1

| Hybridoma name | Bonding to FUT8 by ELISA | FUT8 enzymatic activity (% inhibition) |
|---|---|---|
| 1H9 | Yes | 60% |
| 5C9 | Yes | 87% |
| 1D2 | Yes | 82% |
| 4G1 | Yes | 15% |
| 4A10 | Yes | 15% |
| 4F1 | Yes | 0% |
| 1C4 | Yes | 0% |

Figure 13:
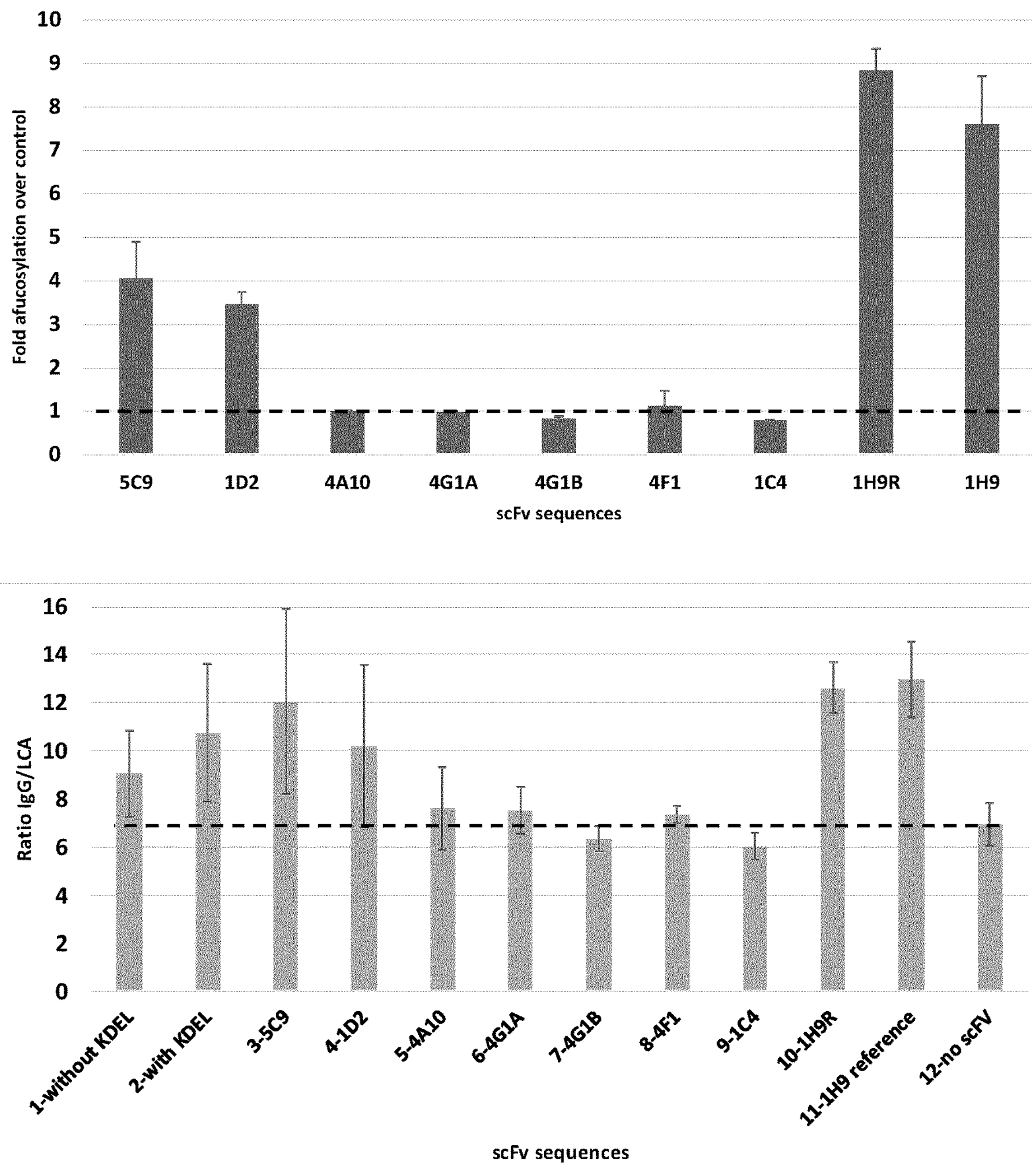
FIG. 13 illustrates that when variable regions of the heavy ($V_H$) and light ($V_L$) chains of the identified hybridoma were introduced into the scFv5 format, cells expressing the identified constructs were able to reduce fucosylation of a co-transfected IgG1 model antibody to various levels compared to the control indicated by the dashed line (upper panel: antibody 1—2G4, an anti-ebola glycoprotein antibody, lower panel: antibody 2—rituximab).

FIG. 13 shows that when the variable regions of the heavy ($V_H$) and light ($V_L$) chains of the selected hybridomas were introduced into the scFv5 format, cells expressing the identified constructs were able to reduce fucosylation of a co-transfected antibody to various levels compared to the control indicated by the dashed line (upper panel: antibody 1—2G4, an anti-ebola glycoprotein antibody, lower panel: antibody 2—rituximab). Especially, the heavy ($V_H$) and light ($V_L$) chain variable regions sequences from the 5C9, 1D2, and 1H9 hybridomas were able to significantly reduce fucosylation (about 4-, 3.5-, and 7.5-8.7-fold, respectively). Variable region sequences which were identified in the in vitro FUT8 activity assay as moderately inhibitory or non-inhibitory (4G1, 4A10, 4F1, 1C4) were also non-significantly inhibitory in this cell based assay. In the context of the scFv2 format, adding a KDEL sequence slightly reduced antibody fucosylation.

| SEQUENCE TABLE | |
|---|---|
| SEQ ID NO: 1 - 1D2 VH | QVQLKESGPGLVAPSQSLSITCTVSGFSLTGYGVN WVRQPPGKGLEWLGMIWGDGSTDYNSALKSRLSIS KDNSKSQVFLKMNSLQTDDTASYYCARDFYDGYLY AMDYWGQGTSVTVSSAS |
| SEQ ID NO: 2 - 1D2 VL | DIVMTQSQKFMSTSLGDRVSVTCKASQNVGSYVAW YQQKPGQSPKALIYSASYRYSGVPDRFAGSGSGTD FTLTISNVQSEDLAEYFCQQYYTYPYTFGGGTWSTR LASWAFRSL |
| SEQ ID NO: 3 - 1D2 VH CDR1 | GPGLVAPSQSLS |
| SEQ ID NO: 4 - 1D2 VH CDR2 | VRQPPGKGLE |
| SEQ ID NO: 5 - 1D2 VH CDR3 | QTDDTASYYCARD |
| SEQ ID NO: 6 - 1D2 VL CDR1 | SQKFMSTSLGDR |
| SEQ ID NO: 7 - 1D2 VL CDR2 | YQQKPGQSPK |
| SEQ ID NO: 8 - 1D2 VL CDR3 | EYFCQQYYTYPYT |
| SEQ ID NO: 9 - 5C9 VH | QVQLKESGPGLVAPSQSLSITCTVSGFSLTGYGVN WVRQPPGKGLEWLGTIWGDGSTDYNSALKSRLSIS KDNSKTQVFLKMHSLQTDDTAIYYCARGGYDDYFG YAMDYWGQGTSVTVSS |
| SEQ ID NO: 10 - 5C9 VL | DIVMTQSQKFMSTVVGDRVSVTCKASQNVGTNVAW YQQKPGQSPKALIYSASYRYSGVPDRLTGSGSGTD FTLTFSYVQSEDLAEYFCQQYYTYPYTFGGGTKLEIK |
| SEQ ID NO: 11 - 5C9 VH CDR1 | GPGLVAPSQSLS |
| SEQ ID NO: 12 - 5C9 VH CDR2 | VRQPPGKGLE |
| SEQ ID NO: 13 - 5C9 VH CDR3 | QTDDTAIYYCARG |
| SEQ ID NO: 14 - 5C9 VL CDR1 | SQKFMSTVVGDR |
| SEQ ID NO: 15 - 5C9 VL CDR2 | YQQKPGQSPK |
| SEQ ID NO: 16 - 5C9 VL CDR3 | EYFCQQYYTYPYT |
| SEQ ID NO: 17 - 1H9 VH | EVQLQQSGPELVKPGASVKMSCKASGYIFTDYVMH WVKQSNGKSLEWIGYINPYNDYSNYNQKFKGKATL TVDKSSNTAYMQLNSLTSEDSAVYFCARSGDVWLA YWGQGTLVTISAAS |
| SEQ ID NO: 18 - 1H9 VL | DIVLTQSPASLAISLGQRATISCRASKSVSTSGYSYM HWYQQKPGQPPRLLIYLASNLESGVPARFSGSGSG TDFTLNIHPVEEEDGATYYCQHSRELPWTFGGGT |
| SEQ ID NO: 19 - 1H9 VH CDR1 | GPGLVAPSQSLS |
| SEQ ID NO: 20 - 1H9 VH CDR2 | VRQPPGKGLE |
| SEQ ID NO: 21 - 1H9 VH CDR3 | QTDDTAIYYCARG |
| SEQ ID NO: 22 - 1H9 VL CDR1 | SQKFMSTVVGDR |
| SEQ ID NO: 23 - 1H9 VL CDR2 | YQQKPGQSPK |

-continued

| SEQUENCE TABLE | |
|---|---|
| SEQ ID NO: 24 - 1H9 VL CDR3 | EYFCQQYYTYPYT |
| SEQ ID NO: 25 - Human fucosyltransferase-8 transmembrane domain | WIMLILFAWGTLLFYIGGHL |
| SEQ ID NO: 26 - Human β4-galactosyltransferase-1 transmembrane domain | LLVAVCALHLGVTLVYYLAG |
| SEQ ID NO: 27 - Human Calnexin transmembrane domain | WLWVVYILTVALPVFLVILFC |
| SEQ ID NO: 28 - endoplasmic reticulum retention signal | KDEL |
| SEQ ID NO: 29- N-Terminal signal peptide | MRLPAQLLGLLMLWVSGSSGDV |
| SEQ ID NO: 30 - C-terminal polyhistidine tag | GGGHHHHHHHHHHG |

The invention claimed is:

1. An alpha-(1,6)-fucosyltransferase (FUT8) antibody, an antigen binding domain thereof, or a fusion protein thereof, comprising a variable region of a heavy chain (VH) and a variable region of a light chain (VL); the antibody, antigen binding domain thereof, or fusion protein thereof being operable to inhibit FUT8 activity in a cell, wherein said VH comprises a CDR1, a CDR2, and a CDR3 comprising the amino acid sequence set forth in SEQ ID NO:3, SEQ ID NO:4, and SEQ ID NO:5, respectively, and said VL comprises a CDR1, a CDR2, and a CDR3 comprising the amino acid sequence set forth in SEQ ID NO:6, SEQ ID NO: 7, and SEQ ID NO:8, respectively; or said VH comprises a CDR1, a CDR2, and a CDR3 comprising the amino acid sequence set forth in SEQ ID NO:11, SEQ ID NO:12, and SEQ ID NO:13, respectively, and said VL comprises a CDR1, a CDR2, and a CDR3 comprising the amino acid sequence set forth in SEQ ID NO:14, SEQ ID NO:15, and SEQ ID NO: 16, respectively; or said VH comprises a CDR1, a CDR2, and a CDR3 comprising the amino acid sequence set forth in SEQ ID NO:19, SEQ ID NO:20, and SEQ ID NO:21, respectively, and said VL comprises a CDR1, a CDR2, and a CDR3 comprising the amino acid sequence set forth in SEQ ID NO:22, SEQ ID NO:23, and SEQ ID NO:24, respectively.

2. The FUT8 antibody, antigen binding domain thereof, or fusion protein thereof of claim 1, comprising a transmembrane domain of a protein resident in: an endoplasmic reticulum (ER), a cis Golgi apparatus, a trans Golgi apparatus, or a combination thereof.

3. A cell expressing the FUT8 antibody, antigen binding domain thereof, or fusion protein thereof of claim 1.

4. A method for producing a recombinant protein or antibody having reduced fucosylation comprising:

a) culturing a host cell expressing the FUT8 antibody, antigen binding domain thereof, or fusion protein thereof of claim 1, wherein said host cell expresses said recombinant protein or antibody under conditions that permit the production of said recombinant protein or antibody; and b) isolating said recombinant protein or antibody.

5. The FUT8 antibody, antigen binding domain thereof, or fusion protein thereof of claim 1, wherein said VH comprises the amino acid sequence set forth in SEQ ID NO: 1 and said VL comprises the amino acid sequence set forth in SEQ ID NO:2.

6. The FUT8 antibody, antigen binding domain thereof, or fusion protein thereof of claim 1, wherein:

said VH comprises a CDR1, a CDR2, and a CDR3 comprising the amino acid sequence set forth in SEQ ID NO:3, SEQ ID NO:4, and SEQ ID NO:5, respectively; and said VL comprises a CDR1, a CDR2, and a CDR3 comprising the amino acid sequence set forth in SEQ ID NO:6, SEQ ID NO:7, and SEQ ID NO:8, respectively.

7. The FUT8 antibody, antigen binding domain thereof, or fusion protein thereof of claim 1, wherein said VH comprises the amino acid sequence set forth in SEQ ID NO: 9 and said VL comprises the amino acid sequence set forth in SEQ ID NO: 10.

8. The FUT8 antibody, antigen binding domain thereof, or fusion protein thereof of claim 1, wherein:

said VH comprises a CDR1, a CDR2, and a CDR3 comprising the amino acid sequence set forth in SEQ ID NO:11, SEQ ID NO:12, and SEQ ID NO:13, respectively; and said VL comprises a CDR1, a CDR2, and a CDR3 comprising the amino acid sequence set forth in SEQ ID NO:14, SEQ ID NO:15, and SEQ ID NO: 16, respectively.

9. The FUT8 antibody, antigen binding domain thereof, or fusion protein thereof of claim 1, wherein said VH comprises the amino acid sequence set forth in SEQ ID NO: 17 and said VL comprises the amino acid sequence set forth in SEQ ID NO: 18.

10. The FUT8 antibody, antigen binding domain thereof, or fusion protein thereof of claim 1, wherein:

said VH comprises a CDR1, a CDR2, and a CDR3 comprising the amino acid sequence set forth in SEQ ID NO:19, SEQ ID NO:20, and SEQ ID NO:21, respectively; and said VL comprises a CDR1, a CDR2, and a CDR3 comprising the amino acid sequence set forth in SEQ ID NO:22, SEQ ID NO:23, and SEQ ID NO:24, respectively.

11. The FUT8 antibody, antigen binding domain thereof, or fusion protein thereof of claim 1, wherein said FUT8 antibody, antigen binding domain thereof, or fusion protein thereof further comprises an endoplasmic reticulum retention signal.

12. The FUT8 antibody, antigen binding domain thereof, or fusion protein thereof of claim 1, which is an IgA, an IgD, an IgE, an IgM, a Fab, an scFv, an scFab, or an sdAb.

13. The method of claim 4, wherein said FUT8 antibody, antigen binding domain thereof, or fusion protein thereof is an scFv.

14. The FUT8 antibody, antigen binding domain thereof, or fusion protein thereof of claim 2, wherein said transmembrane domain is chosen from a transmembrane domain of FUT8, a transmembrane domain of beta-1,4-galactosyltransferase 1 (B4GT1), and a transmembrane domain of human calnexin (hCNX).

15. The FUT8 antibody, antigen binding domain thereof, or fusion protein thereof of claim 14, wherein said transmembrane domain of FUT8 comprises the amino acid sequence set forth in SEQ ID NO:25, said transmembrane domain of B4GT1 comprises the amino acid sequence set forth in SEQ ID NO:26, and said transmembrane domain of hCNX comprises the amino acid sequence set forth in SEQ ID NO:27.

16. The FUT8 antibody, antigen binding domain thereof, or fusion protein thereof of claim 11, wherein said endoplasmic reticulum retention signal comprises the amino acid sequence set forth in SEQ ID NO:28.

* * * * *